US009163869B2

(12) United States Patent
Warhurst et al.

(10) Patent No.: US 9,163,869 B2
(45) Date of Patent: Oct. 20, 2015

(54) TUBE PICKING MECHANISMS WITH AN ULTRA-LOW TEMPERATURE OR CRYOGENIC PICKING COMPARTMENT

(75) Inventors: Julian Warhurst, Ashland, MA (US); Bruce Zandi, Lexington, MA (US); Alexander Carbone, Northridge, MA (US); Frank Hunt, Shrewsbury, MA (US); Robert Cloutier, Lancaster, MA (US); James O'Toole, Franklin, MA (US); Elizabeth Alexander, Shrewsbury, MA (US)

(73) Assignee: Hamilton Storage Technologies, Inc., Franklin, MA (US)

( * ) Notice: Subject to any disclaimer, the term of this patent is extended or adjusted under 35 U.S.C. 154(b) by 730 days.

(21) Appl. No.: 13/193,838

(22) Filed: Jul. 29, 2011

(65) Prior Publication Data

US 2012/0060514 A1 Mar. 15, 2012

Related U.S. Application Data

(60) Provisional application No. 61/381,323, filed on Sep. 9, 2010.

(51) Int. Cl.
*G01N 21/00* (2006.01)
*F25D 13/06* (2006.01)
(Continued)

(52) U.S. Cl.
CPC .............. *F25D 13/06* (2013.01); *F25D 13/04* (2013.01); *G01N 1/42* (2013.01); *G01N 35/0099* (2013.01); *F25D 11/04* (2013.01); *F25D 25/04* (2013.01)

(58) Field of Classification Search
CPC .............................. G01N 35/0099; B01L 9/06
USPC ............................ 422/65, 63, 67, 500, 560
See application file for complete search history.

(56) References Cited

U.S. PATENT DOCUMENTS 5,735,587 A 4/1998 Malin et al.
6,068,437 A 5/2000 Boje et al.
(Continued)

FOREIGN PATENT DOCUMENTS

EP 0725133 12/1998
EP 1074488 9/2002
(Continued)

OTHER PUBLICATIONS

REMP, "Small-Size Store (SSS)", pp. 1-2, http://www.remp.com/index.asp?cms=22.
(Continued)

*Primary Examiner* — Natalia Levkovich
(74) *Attorney, Agent, or Firm* — Andrus Intellectual Property Law, LLP

(57) ABSTRACT

A tube picking mechanism is designed for use in an automated, ultra-low temperature (e.g. −80° C. or −135° C.) or cryogenic (e.g., about −140° C. to −196° C.) storage and retrieval system that stores biological or chemical samples. The samples are contained in storage tubes held in SBS footprint storage racks that are normally stored within an ultra-low temperature or cryogenic freezer compartment. The tube picking mechanism includes a tube picking chamber that is maintained at about −80° C., about −135° C. or at cryogenic temperatures in cryogenic applications. Active electrical and mechanical components are maintained in a compartment above and separate from the refrigerated, ultra-low temperature or cryogenic compartment. Thermal stratification inhibits heat transfer into the lower, ultra-low temperature or cryogenic compartment in which tube picking occurs from the upper compartment in which active electrical and mechanical components are located, and also inhibits heat transfer into the lower, ultra-low temperature or cryogenic compartment via an access door for tube storage racks.

23 Claims, 19 Drawing Sheets

(51) Int. Cl.
*F25D 13/04* (2006.01)
*G01N 1/42* (2006.01)
*G01N 35/00* (2006.01)
*F25D 11/04* (2006.01)
*F25D 25/04* (2006.01)

(56) References Cited

U.S. PATENT DOCUMENTS

| | | | |
|---|---|---|---|
| 6,129,428 | A | 10/2000 | Helwig et al. |
| 6,255,614 | B1 | 7/2001 | Yamakawa et al. |
| 6,397,620 | B1 | 6/2002 | Kelly et al. |
| 6,435,582 | B1 | 8/2002 | DaSilva et al. |
| 6,467,285 | B2 | 10/2002 | Felder et al. |
| 6,478,524 | B1 | 11/2002 | Malin |
| 6,536,859 | B1 | 3/2003 | Bathe |
| 6,568,770 | B2 | 5/2003 | Gonska et al. |
| 6,581,395 | B2 | 6/2003 | Felder et al. |
| 6,688,123 | B2 | 2/2004 | Felder et al. |
| 6,694,767 | B2 | 2/2004 | Junca et al. |
| 6,718,776 | B2 | 4/2004 | Wessling et al. |
| 6,752,479 | B2 | 6/2004 | Ferger et al. |
| 6,941,762 | B2 | 9/2005 | Felder et al. |
| 6,990,819 | B2 | 1/2006 | Darling |
| 7,013,197 | B2 | 3/2006 | Melching et al. |
| 7,013,198 | B2 | 3/2006 | Haas |
| 7,059,138 | B2 | 6/2006 | Bonaquist et al. |
| 7,214,022 | B2 | 5/2007 | Melching |
| 7,227,746 | B2 | 6/2007 | Tanaka et al. |
| 7,290,396 | B2 | 11/2007 | Rampersad et al. |
| 7,314,341 | B2 | 1/2008 | Malin |
| 7,494,168 | B1 | 2/2009 | Miller |
| 7,527,764 | B2 | 5/2009 | Angelantoni et al. |
| 7,635,246 | B2 | 12/2009 | Neeper et al. |
| 7,648,321 | B2 | 1/2010 | Neeper et al. |
| 7,793,842 | B2 | 9/2010 | Neeper et al. |
| 7,861,540 | B2 | 1/2011 | Cloutier et al. |
| 8,083,994 | B2 | 12/2011 | Neeper et al. |
| 8,176,747 | B2 | 5/2012 | Howard et al. |
| 2002/0198610 | A1 | 12/2002 | Malin et al. |
| 2003/0233842 | A1* | 12/2003 | Junca et al. ............ 62/266 |
| 2004/0154322 | A1 | 8/2004 | Felder et al. |
| 2004/0213651 | A1 | 10/2004 | Malin |
| 2004/0258566 | A1 | 12/2004 | Smith |
| 2005/0028538 | A1 | 2/2005 | Darling |
| 2005/0069401 | A1 | 3/2005 | Malin |
| 2005/0188705 | A1 | 9/2005 | Jones et al. |
| 2006/0053825 | A1 | 3/2006 | Owen et al. |
| 2006/0105450 | A1 | 5/2006 | Owen |
| 2006/0289371 | A1 | 12/2006 | Malin |
| 2007/0064383 | A1 | 3/2007 | Tanaka et al. |
| 2009/0101738 | A1 | 4/2009 | Stitt et al. |

FOREIGN PATENT DOCUMENTS

| | | |
|---|---|---|
| EP | 1253817 | 10/2002 |
| EP | 1211197 | 2/2003 |
| EP | 1441026 | 7/2004 |
| EP | 1443101 | 8/2004 |
| EP | 1634496 | 3/2006 |
| EP | 1639892 | 3/2006 |
| EP | 1721964 | 11/2006 |
| EP | 1757883 | 2/2007 |
| EP | 1354028 | 9/2007 |
| EP | 0853657 | 12/2007 |
| EP | 1477813 | 2/2008 |
| JP | 2007-010531 | 1/2007 |
| JP | 2007-30390 | 11/2007 |
| WO | 85/00422 | 1/1985 |
| WO | 98/05753 | 2/1998 |
| WO | 02059251 | 8/2002 |
| WO | 2006074568 | 7/2006 |
| WO | 2006074569 | 7/2006 |

OTHER PUBLICATIONS

REMP, "Tube Punching Module (TPM)", p. 1, http://www.remp.com/index.asp?cms=33, Jan. 2008.
RTS Life Sciences, "RTS A2—Automated Sample Management for Small Libraries/Sample Collections", pp. 1-3, http://www.rtslifescience.com/html/A2-sample-store.htm, Feb. 26, 2009.
LiCONiC AG, "Tube Picker", p. 1, http://www.liconic.com/products/plate-management/plate-manag.html, Jan. 15, 2008.
LiCONiC AG, "Tube Boxer", p. 1, http://www.liconic.com/products/plate-management/tube-boxer.html, Mar. 24, 2009.
The Automation Partnership, "Polar—System Overview", pp. 1-2, http://www.automationpartnership.com/tap/sms/Polar.htm, Mar. 24, 2009.
Matrical Bioscience, "MiniStore", pp. 1-2, http://www.matrical.com/MiniStore.php, Feb. 26, 2009.
Nexus Biosystems, "Universal Store—Compound Storage System", pp. 1-2, http://www.nexusbio.com/Products/SampleManagement/compound_storage.php, Feb. 26, 2009.
TTP Labtech, "comPOUND", pp. 1-2, http://www.ttplabtech.com/products/compound/index.html, Feb. 26, 2009.
Biomicrolab, "XL20 Tube Handler", pp. 1-2, http://www.biomicrolab.com/products_XL20.htm, Feb. 26, 2009.
Honeywell, HIH-400 Series, pp. 1-8, www.honeywell.com/sensing, Minneapolis, MN, Jan. 2007.
RTS Group, "Compound Management", http://rtslifescience.com/html/compound-management.htm, pp. 1-14, 2005, Jan. 15, 2008.
Matrical, "MatriStore—Automated Compound Storage and Retrieval System", "MatriPress—Microwell plate storage freezer rack" http://www.matrical.com/MatriStore2.php, pp. 1-6, Spokane, WA 2007, Jan. 16, 2008.
LiCONiC Instruments, "Product Overview", pp. 1-2, Woburn, MA, Jul. 19, 2007.
Thermo Scientific, "Automated Sample Library at −80C.-Thermo Scientific", http://www.thermo.com/com/dcs/product/detail/10120038,00.html, pp. 1-2, 2007, Jan. 15, 2008.
Tecan Group Ltd.—News, "Automated production of microfluidic devices with the Freedom EVO/REMP Small-Size Store Factory", http://www.tecan.com/page.content/index.asp?MenuID, pp. 1-2, Switzerland, 2008, Jan. 15, 2008.
REMP, "Sample Safe", pp. 1-2, Mannedorf, Switzerland, Jan. 2007.
REMP, "Storage Family", pp. 1-6, Mannedorf, Switzerland, Jan. 2007.
Oriental Motor U.S.A. Corp., "2-Phase Stepping Motor", www.orientalmotor.com, pp. 1-2, Torrance, CA, Jan. 22, 2008.
Applied Motion Products, "Motors, Motion Control Products, Drives and Controls", http://www.applied-motion.com/products/servo/motors/NMseries.php., pp. 1-6, 2006, Jan. 22, 2008.
ANSI/SBS Jan. 2004, "Footprint Dimensions", American National Standards Institute, Society for Biomolecular Sciences, pp. 1-8, Jan. 25, 2006.
AIRTX International, "Air Knives:Aluminum 85000 Series", http://www.airtxinternational.com/catalog/82000/php., pp. 1-4, Jan. 22, 2008.
LiConic Instruments, −80C. Degree Tube Stores, http://liconic.com/products/plate-management/tube-store-80.php, Jul. 10, 2012.
TTPLabTech, Arktic compact, automated biobanking, TTP Labtech strengthens automated sample management for biobanking with arktic: Bringint biobanking to any lab, any size at IQPC, http://ttplabtech.com/news-media/news/ttp-labtech, Jul. 10, 2012.
LiConic Instruments, STC12k5, http:/liconic.com/products/plate-management/tube-store-80.php, Jul. 10, 2012.
LiConic Instruments, STC3k5, http:/liconic.com/products/plate-management/tube-store-80.php, Jul. 10, 2012.
LiConic Instruments, STC7k5, http:/liconic.com/products/plate-management/tube-store-80.php, Jul. 10, 2012.
Matrical Bioscience, NitroStore Mars & Saturn—Biobank/Biorepository, −80C. to −160C. Automated Sample, Storage, Management, & Retrieval Systems, http://matrical.com/Biobank_Biorepsosiory.php, Jul. 10, 2012.
Partial International Search Report, International Patent Application No. PCT/US2011/047732, mailed Jun. 4, 2012.

* cited by examiner

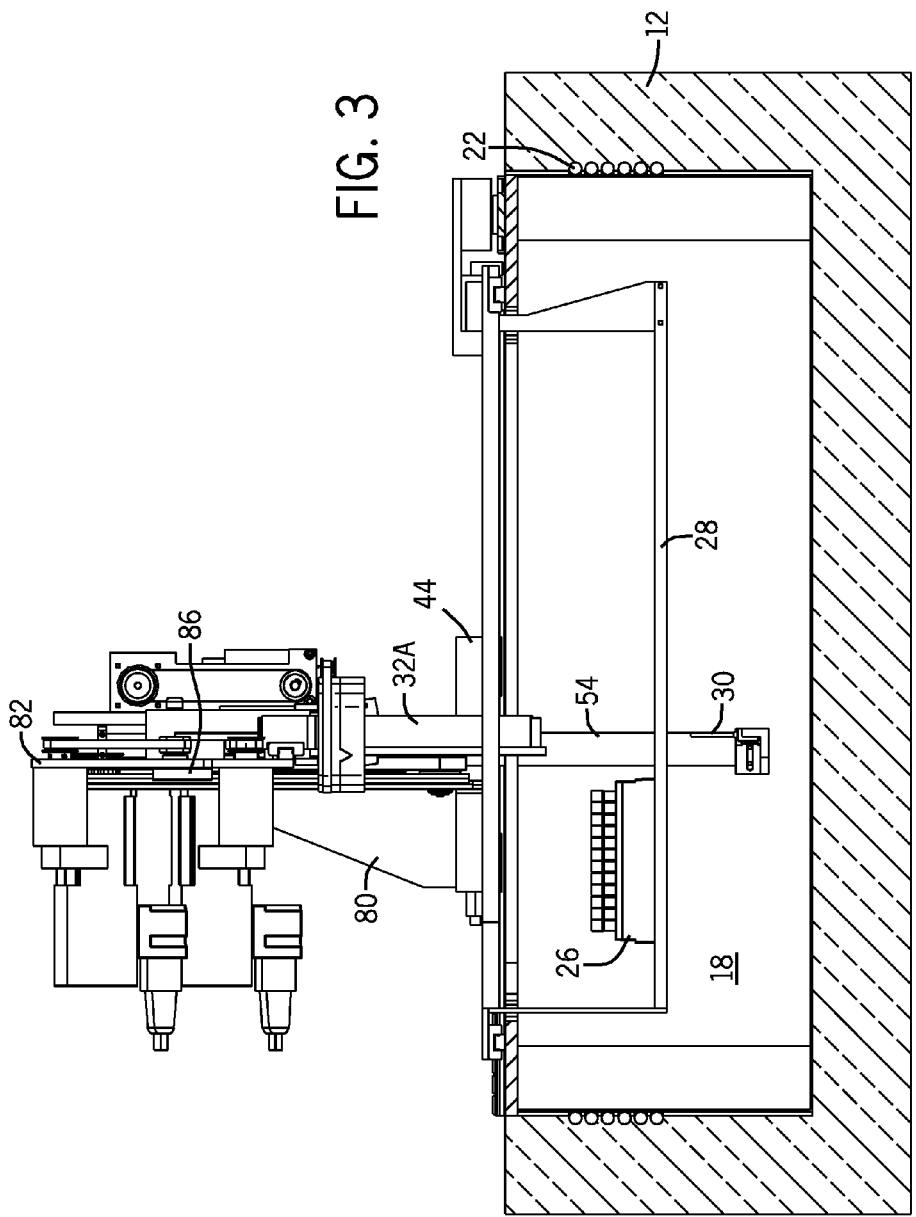

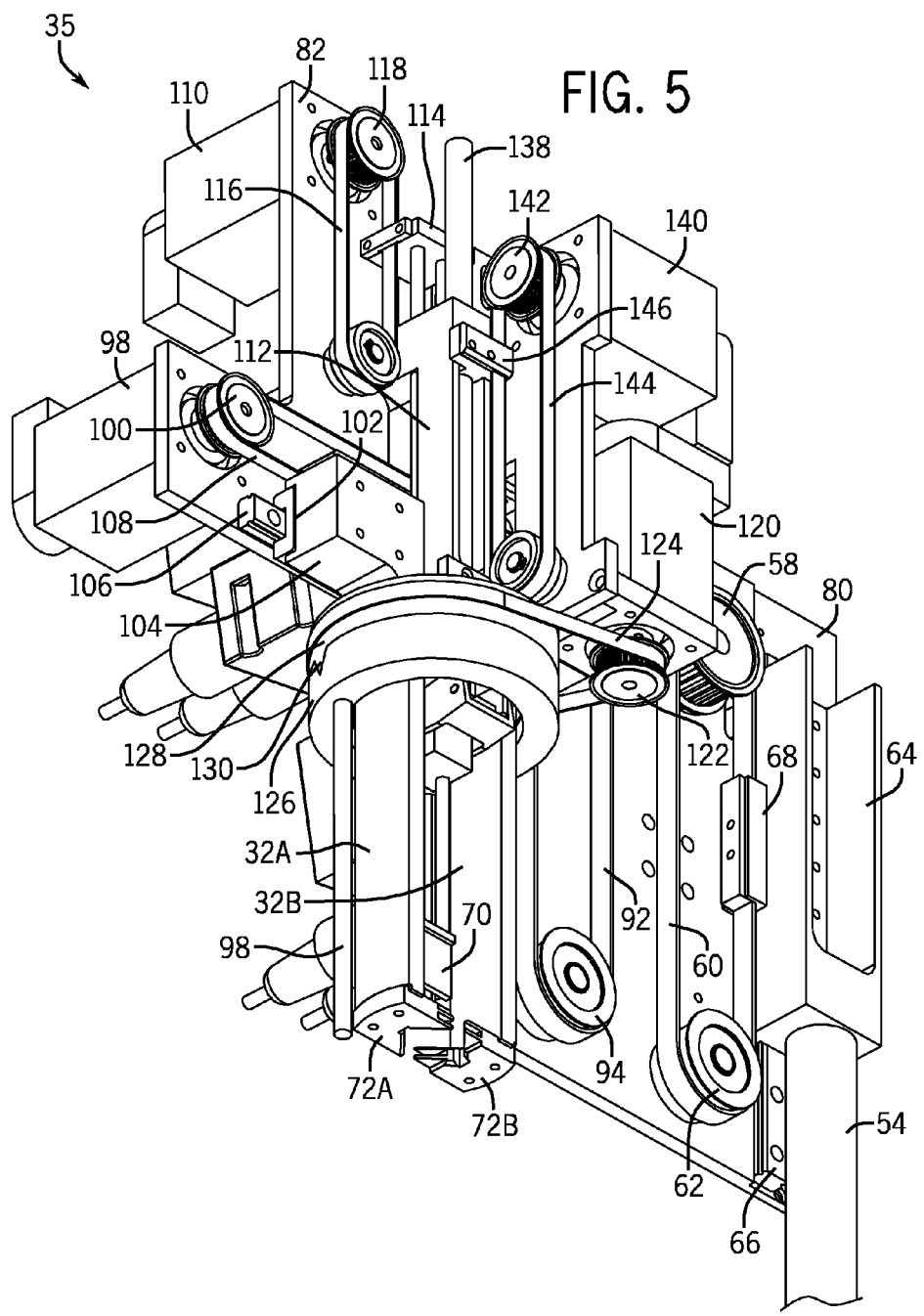

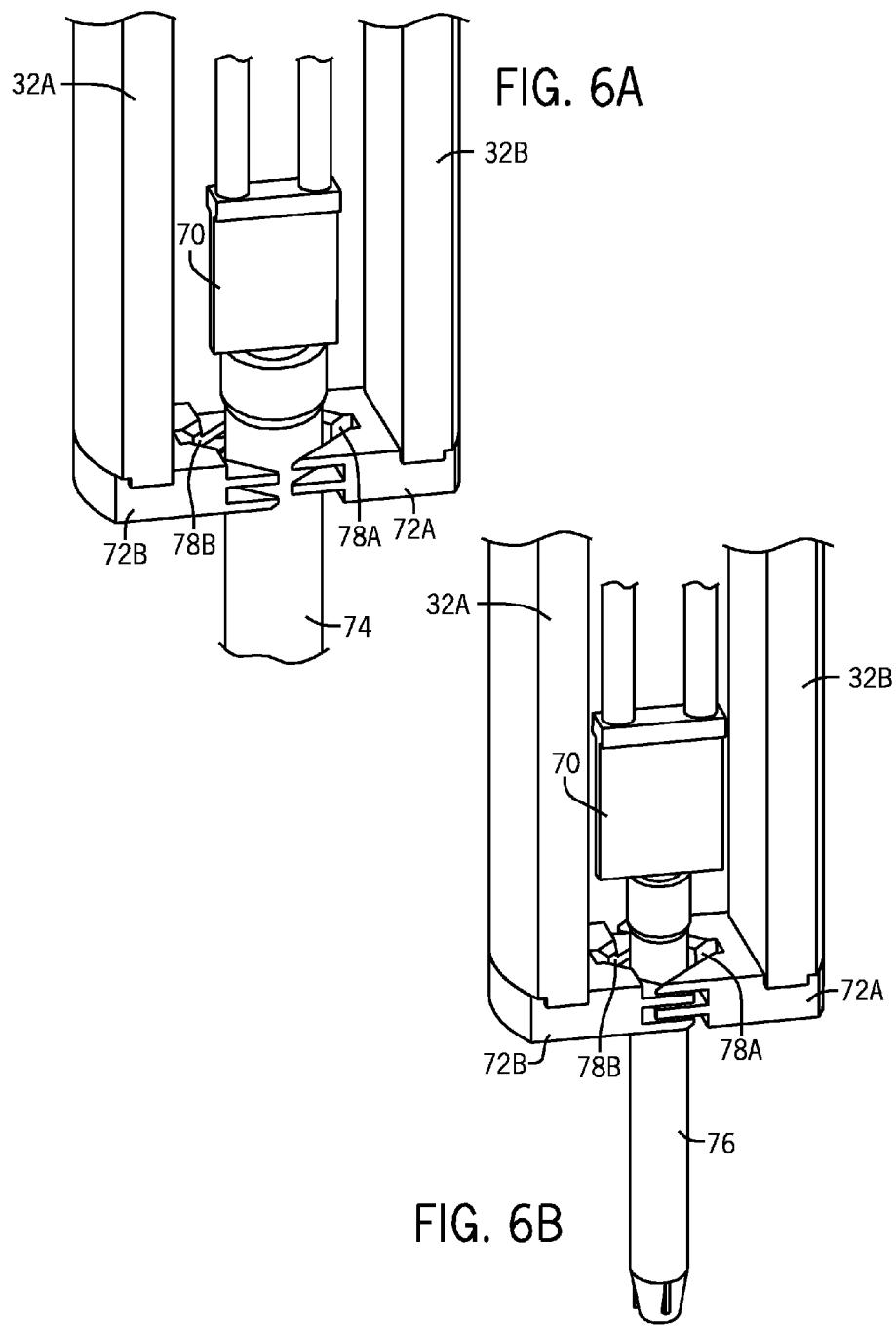

TUBE PICKING MECHANISMS WITH AN ULTRA-LOW TEMPERATURE OR CRYOGENIC PICKING COMPARTMENT

FIELD OF THE INVENTION

The invention is directed to tube picking mechanisms having a tube picking compartment maintained at an ultra-low temperature, e.g. from about −50° C. to about −135° C. or at a cryogenic temperature (e.g., about −140° C. to −196° C.). The tube picking mechanisms are particularly well suited for use in an automated, ultra-low temperature or cryogenic storage and retrieval system used to store and retrieve biological and chemical samples.

BACKGROUND OF THE INVENTION

Storage of biological and chemical samples is becoming widespread in biotechnological and medical industries. Many of these samples must be stored at or below freezing temperatures. Generally speaking, a regular freezer operates from about −5° C. to −20° C., an ultra-low temperature freezer operates from about −50° C. to about −90° C. (preferably at about −80° C.) and a cryogenic freezer operates from about −140° C. to −196° C. (boiling point of liquid nitrogen). For some applications, it is advantageous to store samples below about −120° C. For purposes of this patent application, the term "ultra-low temperature" shall mean temperatures below about −50° C. and above temperatures generally considered to be cryogenic.

Large automated sample storage and retrieval systems that store samples within one or more ultra-low temperature (e.g., −80° C.) or cryogenic (e.g., about −140° C. to −196° C.) freezer compartments are known. Biological samples stored in these systems are often contained in sealed plastic laboratory tubes or vials having a diameter of 3.5 mm or larger. Larger tubes are sometimes called vials in the art, but both are referred herein as tubes, storage tubes or sample storage tubes. The tubes or vials are typically held in storage racks having an array of tube receptacles, for example, 384, 96, 48 or 24 tubes and having openings in the bottom of the tube receptacles. In most cases, a two-dimensional barcode containing identifying information is adhered to the bottom of the storage tube and is able to be read through openings in the bottom of the tube storage racks.

A mechanical robot is often provided to place and retrieve the tube storage racks from the ultra-low temperature or cryogenic freezer compartment. The dimensions of the tube racks are typically SBS footprint compatible, but the tubes often have a variety of dimensions. The robot interacts with an I/O module in order to introduce samples into the system from the ambient environment and to retrieve samples for use outside of the system. The freezers typically have trays, shelves or cassettes for several hundred or even thousands of tube storage racks. It is not normally desirable to remove an entire SBS tube rack from the system through the I/O module when only one or a few tubes from a given storage rack are desired to be retrieved. The removal procedure may allow for the ingress of moisture into the system, and also renders the other samples held in the same tube rack susceptible to warming and thawing, at least partially, even if the tube rack is removed from the system temporarily. Robotic tube picking mechanisms are used in some systems to pick individual tubes for retrieval from the system. Even pulling storage racks from an ultra-low temperature or cryogenic freezer in order to pick tubes in a refrigerated, yet warmer environment, such as −20° C. or −30° C., can also allow undesirable warming of samples.

While tube picking mechanisms are generally known in the art, the environment within an ultra-low temperature or cryogenic freezer compartment is typically too cold to ensure reliable operation of conventional tube picking mechanisms. One issue is that the electrical, pneumatic and hydraulic components are unreliable at such ultra-low temperatures. Also thermal expansion and contraction of robotic components and storage racks can cause significant mechanical difficulties if not properly addressed. Another issue is that the formation of frost and ice is exacerbated due to the low moisture saturation point in ultra-low temperature or cryogenic environments. At such low temperatures, the air can hold very little moisture so any moisture introduced into the freezer environment tends to form frost on the cold surfaces within the environment. Frost and ice accumulation can interfere with the removal of tubes from racks and with the insertion of tubes into the racks. In addition, the moving parts of a tube picker in the freezer environment can become contaminated with ice and cause mechanisms to jam.

To date, tube picking mechanisms have been commercially used in low temperature (e.g. −20° C.) environments, but as mentioned it is difficult or impractical to operate a tube picking mechanism in ultra-low temperature or cryogenic environments. For this reason, some commercial systems compromise and place the ultra-low temperature or cryogenic freezers within a refrigerated −20° C. enclosure and pick sample tubes from the racks in the −20° C. environment. However, as mentioned previously, exposure of samples even to a −20° C. environment may cause undesirable warming.

The present invention is directed to tube picking mechanisms that are particularly well suited for use in an automated ultra-low temperature (e.g., −80° C. or −135° C.) or cryogenic storage and retrieval system. An object of the present invention is to provide a system that can efficiently and reliably pick selected tubes from storage racks within a tube picking chamber maintained at ultra-low (e.g. −80° C. or −135° C.) or cryogenic (e.g., about −140° C. to −196° C.) temperatures. Another object is to provide a system that also efficiently and reliably transfers tubes picked from retrieved source racks to a destination rack in an ultra-low temperature or cryogenic environment so that the selected tubes are ready for export from the system.

SUMMARY OF THE INVENTION

In order to meet these objectives and others, the invention provides a tube picking mechanism having a tube picking chamber that is maintained at an ultra-low temperature (e.g., −50° C. to −90° C. or colder e.g., about −135° C.) or at a cryogenic temperature (e.g., about −140° C. to −196° C.). The exemplary embodiments of the tube picking mechanism described herein have a lower compartment cooled to an ultra-low temperature (e.g., about −80° C.), which will normally be desirable if the tube picking mechanism is being used in connection with a system having ultra-low temperature (e.g., having a refrigeration set point of −80° C.) freezers to store samples. It is optimal to that the temperature of the tube picking chamber be at or near the temperature of the storage freezers in the system. For example, it would normally be desirable to cool the tube picking chamber to a cryogenic temperature (e.g., about −140° C. to −196° C.) if the samples are stored at a cryogenic temperature or to an ultra-low temperature of about −135° C. if the samples are stored at about −135° C. or colder.

The tube picking mechanism also includes an upper compartment in which the temperature is warmer (e.g. preferably about −20° C. to −30° C.) than the temperature (e.g. −80° C.)

of the lower compartment in the tube picking chamber. The bottom portion of the upper compartment is adjacent to the top portion of the lower compartment forming a warm-cold boundary therebetween. Tube picking is accomplished in the lower ultra-low temperature (e.g. −80° C.) or cryogenic compartment whereas active mechanical and electrical components are housed in the warmer, upper compartment. Structural components pass from the warmer, upper compartment into the ultra-low temperature or cryogenic lower compartment in order to enable movement of mechanical components necessary to pick tubes from storage racks. Thermal stratification helps to maintain the ultra-low or cryogenic temperature of the refrigerated, lower compartment without the need for sealing along the warm-cold boundary between the upper compartment and the lower compartment. It is desirable that components passing from the upper compartment into the ultra-low temperature or cryogenic lower compartment be made of insulating materials with low thermal conductivity.

In the preferred embodiment of the invention, the tube picking mechanism includes a picker plate located in the ultra-low temperature or cryogenic, lower compartment. The picker plate holds at least one tube storage rack and preferably has nesting locations for several storage racks. Each storage rack nest on the picker plate preferably has an opening that allows access from below the picker plate to the bottom side of the storage rack placed on the plate. Storage rack nests for destination racks, as contrasted to source racks, do not necessarily require access from below the picker plate. At least one door is provided along the upper surface of the lower compartment to allow robotic access for placing and retrieving storage tube racks into the refrigerated, ultra-low temperature or cryogenic lower compartment. The location of the door utilizes thermal stratification to reduce the heat gain when opening and closing the door.

The tube picking mechanism includes a picker head preferably having a pair of gripping fingers that extend vertically downward into the refrigerated, ultra-low temperature or cryogenic, lower compartment. The preferred gripping fingers have intermeshing gripping jaws at their distal end to facilitate the gripping and lifting of a single tube from a receptacle in a tube storage rack located on the picker plate. It is preferred that the gripping jaws have an intermeshing configuration so that they are able to engage storage tubes of different diameters. In the upper compartment, the tube picking mechanism contains a motorized mechanism to open and close the gripping fingers, and another motorized mechanism to lift and lower the gripping fingers. The picker head also includes a mechanism for clearing a tube from the jaws or ensuring the tube is fully inserted into the rack, known as a "shucking" mechanism. Preferably, a shucking head or piston is located between the gripping fingers and is movable vertically by a motor located in the upper compartment such that the shucking head is able to move independently of the gripping fingers. The gripping jaws at the end of the gripping fingers preferably include slots through which the shucking head may pass in order that the shucking head can push tubes when the jaws are open completely into the storage rack flush with the other tubes in the storage rack.

The tube picking mechanism also preferably includes a presenter push pin that is located in the refrigerated, ultra-low temperature or cryogenic, lower compartment below the picker plate. The presenter push pin is aligned vertically with the pair of gripping fingers. Appropriate upward vertical movement of the presenter push pin pushes on the bottom of a selected storage tube in a tube rack on the picker plate to lift the tube and present it to the gripping fingers to grip and lift the storage tube from the tube rack. A motorized drive mechanism for the presenter push pin is provided in the warmer, upper compartment.

It is preferred that the upper compartment be enclosed with a non-thermally insulated vapor barrier. It is desirable that the heat generated by the active electrical and mechanical components in the upper compartment dissipate to the surrounding environment. On the other hand, it is important to prevent moisture from entering into the tube picking mechanism in order to reduce ice and frost formation.

In one desirable embodiment, the picker plate is a rotary picker plate having several storage plate nesting locations spaced circumferentially around the plate. A rotary drive mechanism is provided in the warmer, upper compartment to rotate the picker plate so that the desired nesting location is located beneath the gripping fingers of the tube picking head. It is desirable for the rotary picker plate to also include a biasing corner reference mechanism, such as spring loaded biasing fingers, adjacent to each nest for the purpose of corner referencing the storage rack in a known fixed position within the nest. This is important because the nest dimensions need to be large enough to accommodate a number of different types of storage racks that may have somewhat different dimensions. It has been found that even SBS format storage racks have somewhat different dimensions especially when cooled to ultra-low or cryogenic temperatures. The biasing mechanism not only reduces movement of the racks during operation but also locates the rack in a precise corner referenced position which facilitates reliable tube picking. It is further desirable that the system include a motorized release mechanism to mechanically release the corner reference mechanism in order to enable the placement and removal of storage tube racks in the respective nesting locations. Preferably, this is accomplished with a motorized rotary drive located in the warmer, upper compartment, which turns a downwardly extending rod having a rotating finger that mechanically moves the corner reference mechanism against the direction of bias.

Another embodiment of the invention uses a Cartesian picker plate instead of a rotary picker plate. In this embodiment of the invention, a linear drive mechanism is provided in the upper compartment to move the tube picking head horizontally in one Cartesian direction. Another linear drive mechanism is provided in the upper compartment to move the picker plate mechanism horizontally in a perpendicular Cartesian direction. These linear drive mechanisms allow the tube picking head to access all of the tubes in all the storage racks on the picker plate. The embodiment of the invention having a rotary picker plate, on the other hand, also has linear drive mechanisms to move the tube picking head into alignment with tubes in the storage rack located beneath the gripping jaws of the picker head but the horizontal range of motion of the picker head in the rotary embodiment is substantially less than in the Cartesian embodiment. The smaller range of motion enables the rotary embodiment to have less open area in the partition plate between the upper and lower compartments.

Preferably, the picker head includes a clamping mechanism for holding the storage rack on the picker plate during the tube picking process. One suitable clamping mechanism uses a clamp hold down rod located on the picker head that is movable vertically and is also capable of being placed at a location circumferentially spaced from the gripping fingers. The preferred rack clamp, however, is mechanically separate from the picker head. It includes a pair of independently positionable clamping feet which in use are positioned in predetermined locations in a substantially horizontal plane against the top surface of the storage rack or hovering slightly above the top surface of the storage rack when the rack is located in a nesting location on the picker plate beneath the gripping fingers of the picker head. It can be difficult to find suitable clamping locations on the top surface of the racks which will not interfere with tubes located in the racks or the removal or placement of tubes within tube receptacles in the racks. Given that there are a wide variety of tube storage racks and tube sizes and configurations, it is very likely that a desirable clamping location for one type or model of tube storage rack will be ineffective or inappropriate for another type or model of tube storage rack. Therefore, in accordance with this aspect of the invention, the predetermined clamping locations for the independently positionable clamping feet are preselected for the type or model of storage rack that is located in the respective nesting location on the picker plate. The positions of the clamping feet in the horizontal X-Y plane are repositionable depending on the type or model of storage rack that is being clamped. Desirably, the control system stores data regarding optimum clamping locations of each independently driven clamping feet for multiple types or models of storage racks. As with the other mechanical components of the system, it is desirable that the clamp drive mechanisms be located in the upper, warmer compartment. Preferably, the clamping feet are attached at the distal end of downwardly extending legs which are driven independently along an X-axis and Y-axis of a substantially horizontal plane. On the other hand, since the height of any given tube rack is generally a known constant. Accordingly it will typically be possible to use a common Z-axis drive mechanism to lift and lower the clamping feet and legs in unison.

The preferred system is able to detect the presence of a selected tube between the gripping jaws prior to closing. The encoder for the servomotor driving the shucking mechanism can be used to sense the presence of a storage tube between the gripping jaws prior to closing the gripping fingers. The preferred system is also able to detect the diameter of a tube engaged in the gripping jaws. The servomotor for opening and closing the jaws is preferably set at a torque output that is sufficient to securely engage storage tubes when gripping the storage tubes but insufficient to continue closing when a tube is located between the jaws. The encoder on the servomotor for opening and closing the gripping fingers therefore can be used to detect the diameter of the storage tube within the gripping jaws. The system can then compare the detected diameter to the diameter that was expected for the selected tube.

As emphasized above, depending on the specific application in which the invention is used, it may be desirable to maintain the temperature in the lower compartment at a cryogenic temperature or at an ultra-low temperature below −50° C. such as −580° C. or −135° C. It should also be mentioned that various aspects of the invention are well suited for applications other than the described split temperature application. For example, various aspects of the picker head or clamping mechanisms are suitable for use in other applications.

Other features and advantages of the invention may be apparent to those skilled in the art upon reviewing the following drawings and description thereof.

BRIEF DESCRIPTION OF THE DRAWINGS

FIG. 3 is a sectional view taken along line 3-3 in FIG. 2.

FIG. 5 is a detailed view of a tube picking head in the tube picking mechanism in FIG. 1.

FIGS. 6A and 6B are detailed views of the gripping jaws used in accordance with the first embodiment of the invention.

DETAILED DESCRIPTION

Figure 1:
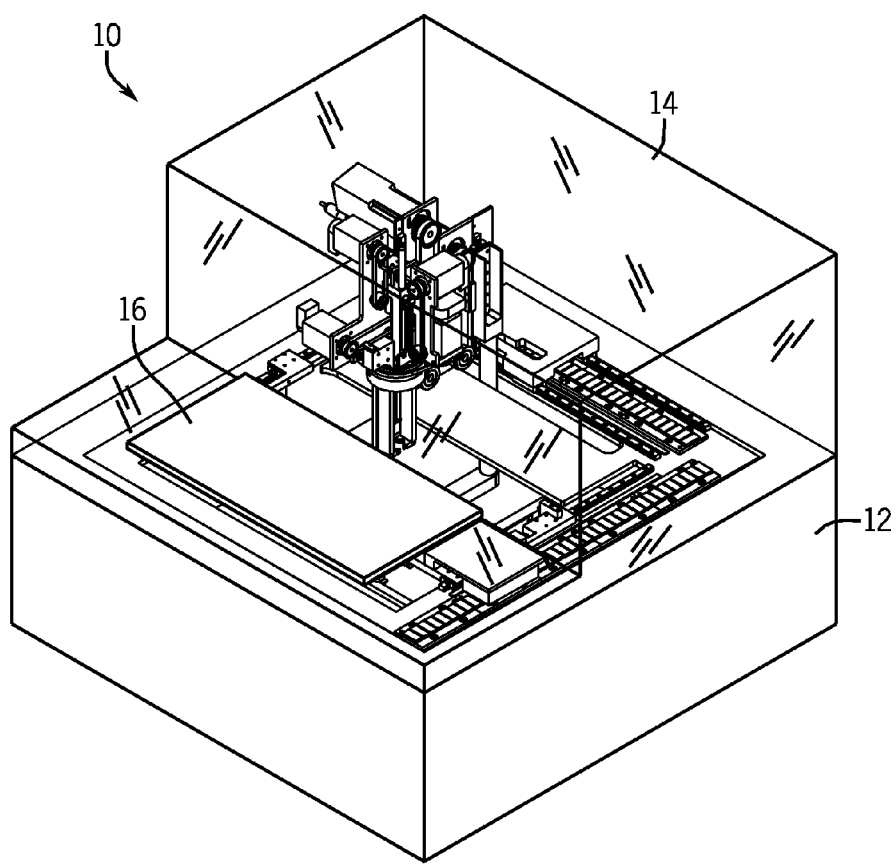
FIG. 1 is a perspective view of a tube picking mechanism constructed in accordance with a first embodiment of the invention.

FIG. 1 is a perspective view of a tube picking mechanism 10 that is constructed in accordance with a first exemplary embodiment of the invention. The tube picking mechanism shown in FIG. 1 includes a chamber 12 that is refrigerated to an ultra-low temperature (e.g., below −50° C. and desirably about −80° C. in most non-cryogenic applications) when the tube picking mechanism 10 is in operation. The tube picking mechanism is designed to be used to pick tubes from racks stored in an ultra-low temperature freezer system. In a typical ultra-low temperature application (e.g., about −80° C.) it is desirable that the temperature of the refrigerated chamber 12 be cooled to the temperature or near the temperature at which samples are stored in the system freezers; however, the invention is not limited to this condition. For example, as mentioned above in the event that the tube picking mechanism is used in connection with a cryogenic freezer system, it will normally be desirable to cool the chamber 12 to cryogenic temperature or, alternatively, to about −135° C. In applications with storage at cryogenic temperatures or an ultra, ultra-low temperatures (such as −135° C.), it may be desirable to maintain the sample temperature when picking tubes below about −120° C. because below this temperature ice crystals do not generally change shape. As mentioned, however, the exemplary embodiments of the invention shown in the figures have a lower chamber 12 that is refrigerated to an ultra-low temperature preferably of about −80° C.

An SBS format tube storage racks are shuttled into and retrieved from the compartment 18 (see, e.g., FIG. 4) within the refrigerated chamber 12 and tube picking occurs within the compartment 18 in the refrigerated chamber 12. A door 16 is provided to allow the insertion and retrieval of SBS tube storage racks into and from the compartment within the refrigerated chamber 12.

The tube picking mechanism 10 also includes a vapor barrier 14 that encloses an upper compartment 20 (see, e.g., FIG. 4) in which the temperature is kept warmer than the ultra-low temperature (e.g. −80° C.) in the lower compartment. A fundamental issue with ultra-low temperature (e.g. −80° C.) or cryogenic storage and picking of sample tubes is frost and ice formation. Frost and ice can interfere with removal of tubes from the rack and insertion of tubes into the rack. In addition, moving parts of the tube picking mechanism can become contaminated with ice causing the mechanism to jam. Therefore, it is desirable to take precautions, such as using a vapor barrier 14, to minimize moisture ingress into the compartments 18 and 20.

Figure 4:
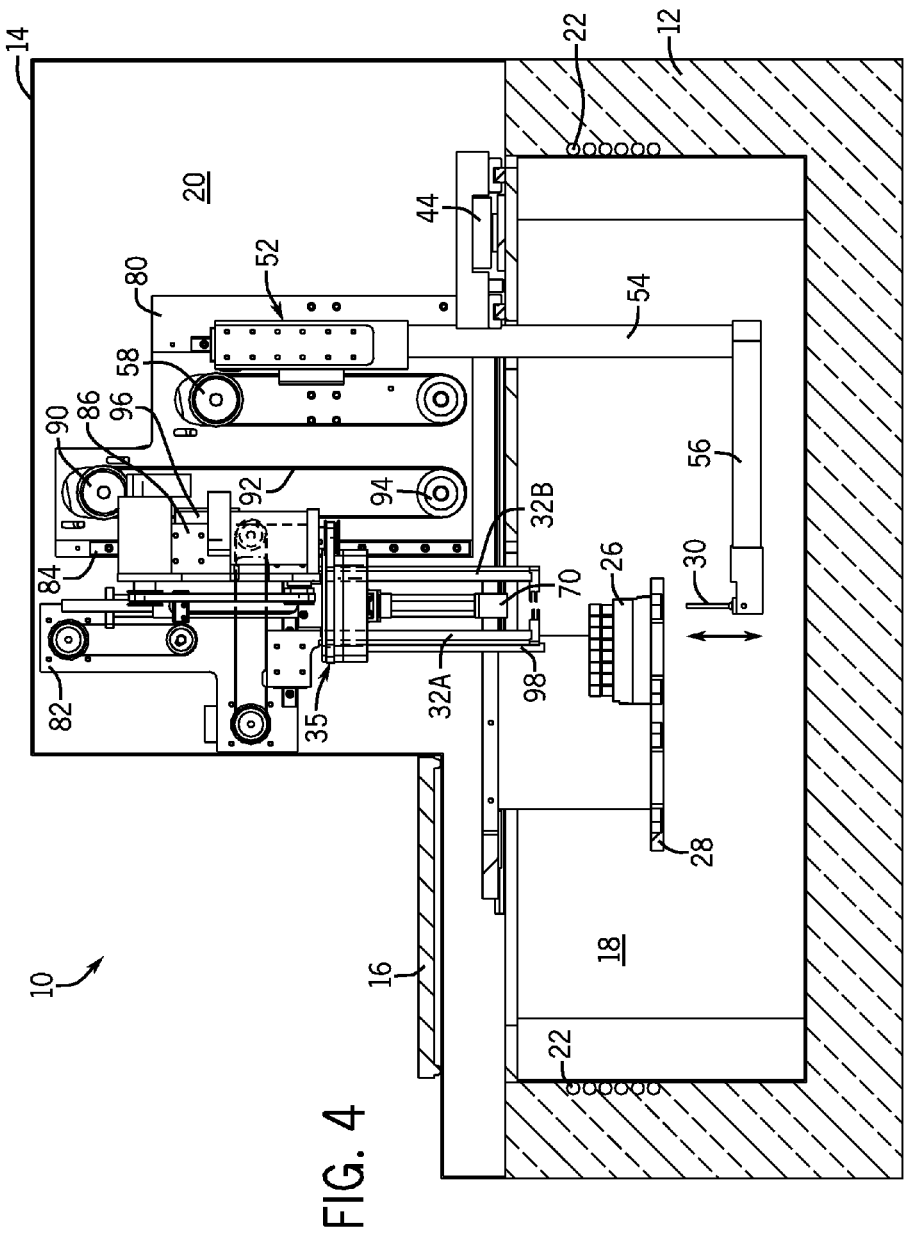
FIG. 4 is a sectional view taken along line 4-4 in FIG. 2.

Referring now to FIG. 4, the tube picking mechanism 10 includes an upper compartment 20 surrounded by the vapor barrier 14 and a lower compartment 18 contained within the refrigerated chamber 12. The active electrical and mechanical components of the tube picking mechanism 10 are contained in the upper compartment 20, whereas tube picking occurs in the lower compartment 18 maintained at the ultra-low temperature (e.g., −80° C.). Refrigeration coils 22 are wrapped around the sidewalls of the refrigerated chamber, and the sidewalls and the bottom wall of the refrigerated chamber 12 are insulated. In particular, referring briefly to FIG. 2, the lower compartment (see reference number 18 in FIG. 4) is contained within a refrigerated liner 48, and refrigeration coils 22 are wrapped around the sidewall of the liner 48. The liner 48 and the coils 22 are encased in a foam or vacuum panel insulation 50.

Still referring to FIG. 4, the temperature in the upper compartment 20 is warmer than the ultra-low temperature in the lower compartment 18, and preferably held at about −20° C. to −30° C. The vapor barrier 14 is preferably made of a thermally conductive material such as aluminum. This allows the heat of the mechanical components generated by the picker mechanism (motors, electronics, etc.) to be dissipated to the room environment and therefore does not present a heat load to the refrigeration unit for the lower chamber 12. The upper compartment 20 is situated above the lower compartment 18, and the tube picking mechanism 10 takes advantage of thermal stratification that occurs naturally in the uncirculated air space of the lower compartment 18 in order to minimize heat transfer from the upper compartment 20 into the lower compartment 18. A partial physical partition 24 made of aluminum with a lower layer of thermal insulation, is located between the top of the lower chamber 18 and the bottom of the upper chamber 20. The physical partition 24 forms a portion of a warm-cold boundary between the upper compartment 20 and the lower compartment 18. While it is necessary to provide openings through the partition 24 in order to allow access for mechanical components of the tube picking mechanism to pass from the upper compartment 20 to the lower compartment 18, it has been found that, due to thermal stratification, thermal loss from the lower compartment 18 is rather insignificant even without providing seals. Nevertheless, it is desirable to keep the size of the openings in the partition 24 at a minimum.

It is desirable that the temperature in the upper compartment 20 be maintained at a temperature higher than −40° C. in order to facilitate proper operation of electrical and mechanical components. In an application in which the tube picking mechanism 10 is used within an environment maintained at −20° C., it is expected that the temperature within the upper compartment 20 will be in the range of −30° C. to −20° C. Desirably, the partition 24 is made of an aluminum plate with a thermally insulating material attached to it. It is also desirable to make components spanning from the upper compartment 20 into the lower compartment 18 of thermal insulating materials in order to reduce heat conduction from the upper compartment 20 into the lower compartment 18. Further, there is an advantage to operating in the upper compartment 20 at a relatively low temperature, e.g. −20° C. to −30° C., rather than normal lab conditions of 25° C. in order to reduce heat transfer from the upper compartment 20 to the lower compartment 18 in all forms including radiation and conduction.

Thus, the tube picking mechanism 10 provides a dual environment: a lower compartment 18 maintained at an ultra-low temperature (e.g. −80° C.) for holding tube racks of samples and picking the tubes from the racks, and an upper compartment 20 maintained at a warmer temperature in which the active electrical and mechanical components reside. FIG. 4 shows a rack 26 of storage tubes residing on a picker plate 28 within the ultra-low temperature compartment 18. Once the rack 26 is delivered, the samples are not exposed to the warmer space in the upper compartment 20 during the tube picking process until it is time to return the rack 26 to storage after tube picking is complete.

Figure 2:
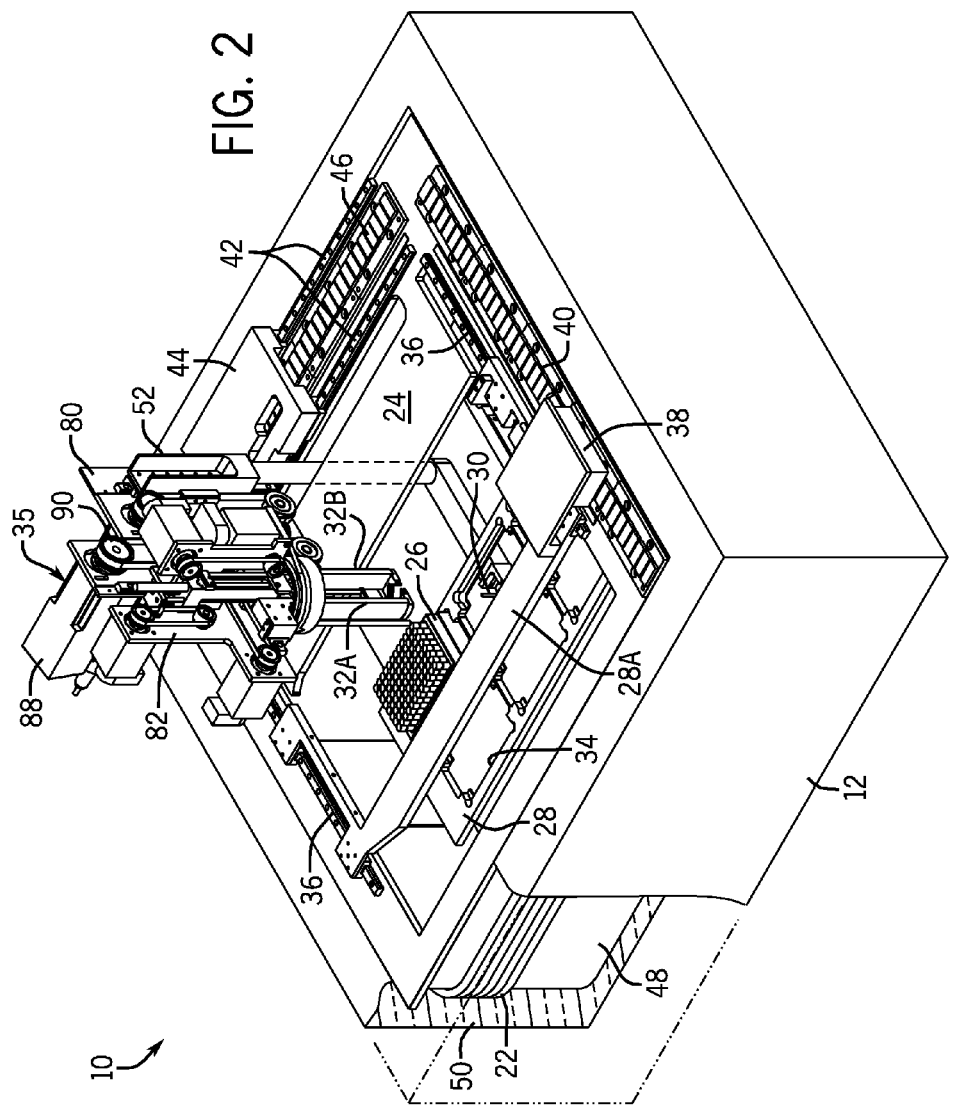
FIG. 2 is a perspective view similar to FIG. 1 with certain parts removed or broken away in order to depict additional components of the tube picking mechanism shown in FIG. 1.
Figure 2A:
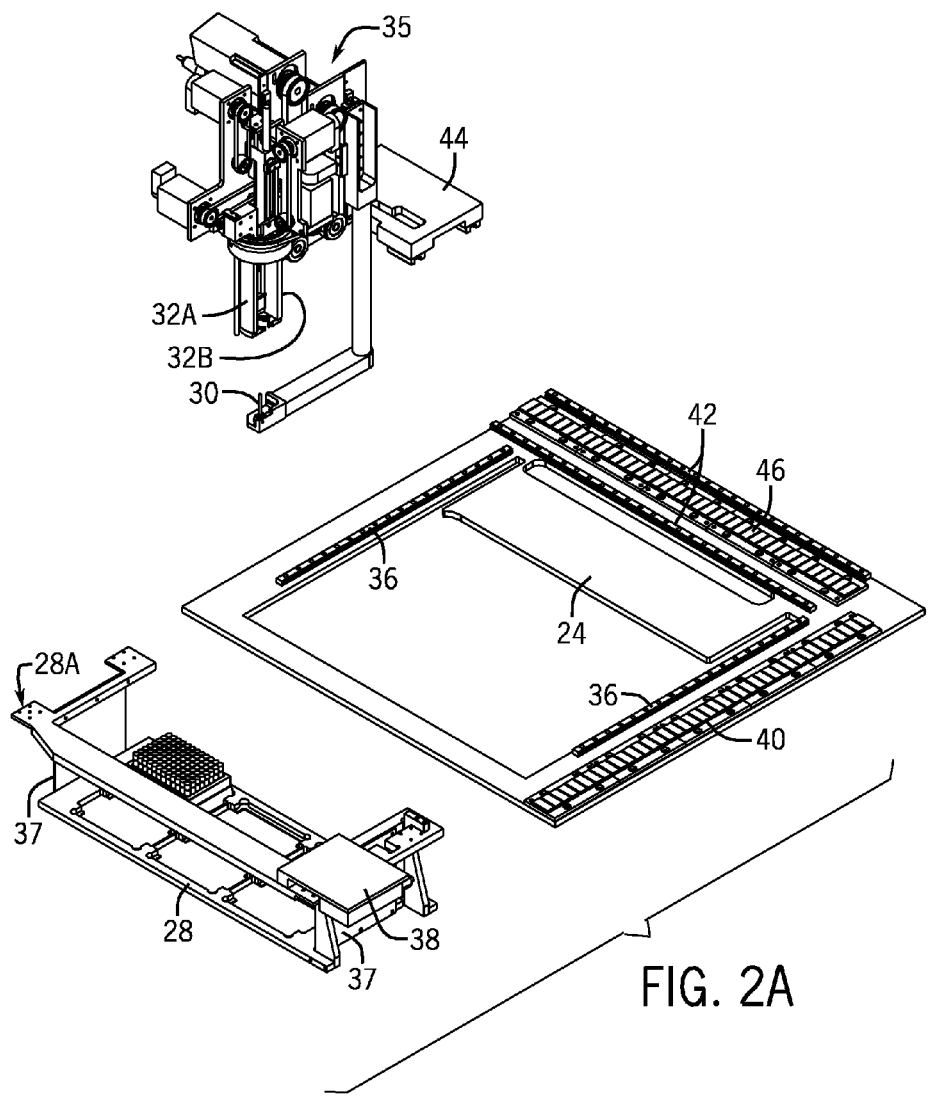
FIG. 2A is an exploded view of various components of the tube picking mechanism shown in FIG. 1.

Referring generally to FIG. 2, the tube picking mechanism 10 includes a picker plate 28, a presenter push pin 30 and a pair of gripping fingers 32, each driven by one or more servomotor drive mechanisms. In some applications, depending on the design of the gripping fingers 32, the system may not require a presenter push pin 30. The picker plate 28 shown in FIG. 2 includes two rows of three receptacles for receiving tube racks 26. Normally, the system will be operated with at least two racks 26 being located on the picker plate 28 wherein at least one of the racks 26 is a destination rack and one of the racks is a source rack. The rack nesting receptacles 34 in the picker plate 28 each include an opening that allows the presenter pusher pin 30 physical access to each tube location in the storage rack 26. Most conventional tube racks include an opening below the respective tube receptacle in the rack to provide both physical and visual access to the bottom of the tubes when stored in the storage rack 26. Referring also to FIG. 2A, the picker plate frame 28A moves linearly along rails 36 mounted on a top surface of the partition 24. Linear drive motor 38 moves the picker plate assembly 28A horizontally along track 40 on the partition plate 24 in one Cartesian direction. It is desirable that the side arms 37 of the picker plate assembly 28A be made of a material with low thermal conductivity such as insulated fiberglass composite material.

Still referring to FIGS. 2 and 2A, a tube picking head 35 includes at least two gripping fingers 32 and the servo drive mechanisms for the gripping fingers 32, as well as the presenter pusher pin 30 and the servo drive mechanism for the presenter push pin 30. The tube picking head 35 in this embodiment of the invention is mounted on rails 42 that are situated horizontally on the partition plate 24 in a direction perpendicular to the direction of the rail 36 for the picker plate frame 28A. A linear servo motor 44 drives the tube picking head 35 along the track 46 located between the rails 42. Note that various alternative drive mechanisms for the picker head and the picker plate may be suitable for implementing various aspects of the invention. For example, it may be desirable to situate one or more of the horizontal drive tracks so that the parallel rails are vertically displaced from on another. Also, as explained in connection with FIGS. 11 through 18, it may be desirable to replace the Cartesian system with a system having a rotary picker plate.

Various types of cooling circuits can be used to provide chilled refrigeration to the refrigeration coils 22. One desirable cooling system comprises what is typically a second stage compressor unit of a two-stage ultra-low temperature cooling unit. This cooling system is appropriate when the tube picking mechanism 10 is located within a −20° C. to −30° C. environment. The second stage compressor cools the coils to approximately −86° C. and dissipates the waste heat in the −20° C. environment. A suitable second stage compressor is the CF04K6E model which can be purchased from Copeland. As a practical matter, cooling the chamber 12 below about −86° C. will normally require the use of liquid nitrogen.

Alternatively, the second stage compressor unit can be used to pre-cool compressed air from −20° C. to −50° C., and a vortex cooler can be used to cool the air from about −50° C. to −100° C. A suitable vortex cooler is manufactured by Vortek. In such an arrangement, the refrigerant is dry compressed air, preferably provided at room temperature and 150 psi. If the tube picking mechanism is located in a −20° C. environment, it is preferred that the compressed air line pass through a heat exchanger in the −20° C. environment in order to drop the temperature of the compressed air from room temperature to about −20° C. prior to passing the compressed air to the second-stage compressor unit and the vortex cooler. As another alternative, a Peltier cooler can replace the second-stage compressor unit to drop the temperature from about −20° C. to about −50° C. Other cooling system arrangements may be suitable and can be used without departing from the spirit of the invention (e.g., a liquid nitrogen cooling system, or Sterling engine).

Referring now to FIGS. 2 through 5, the presenter push pin 30 is positioned under the tube rack 26 on the picker plate 28, and is vertically oriented and in vertical alignment with the pair of gripping fingers 32. The presenter push pin 30 pushes tubes from the bottom and out of the rack 26 with upward vertical motion. A presenter drive mechanism 52, FIG. 4, is located in the upper compartment 20. An insulated rod 54, preferably a hollow drive rod, connects the drive mechanism 52 to an arm 56 on which the presenter push pin 30 is mounted. The presenter drive mechanism 52 is driven by a servomotor (not shown) which turns a drive wheel 58. A drive belt 60 is mounted over the drive wheel 58 and an idler wheel 62. The insulated drive rod 54 is connected to a linear bearing bracket 64 that is mounted on vertical rail 66, FIG. 5. The bearing bracket 64 is clamped to the drive belt 60, see clamp 68, FIG. 5. The bearings, belt and motor driving the drive rod 54 for the presenter push pin 30 are all isolated from the refrigerated, ultra-low temperature compartment 18. The use of a hollow, thermally insulating drive rod 54 minimizes heat conduction into the refrigerated compartment 18 while providing structural rigidity.

Gripping fingers 32A, 32B on the picker head 35 reach down from the upper compartment 20 into the lower, refrigerated ultra-low temperature compartment 18. The gripping fingers 32A, 32B pick a selected tube from the tube rack 26 after it has been presented by the presenter push pin 30. A present push pin 30 may not be necessary if the gripping fingers are suitably slender to reach between the tubes. The gripping fingers 32A, 32B are preferably made of a low thermal conductivity structural plastic such as polyetherimide (PEI).

The picker drive mechanisms are mounted generally to a vertical base frame 80 and a secondary vertical plate 82, FIG. 2. Vertical base frame 80 is rigidly connected to the linear bearing 44, and is movable in the horizontal direction but stationary in the vertical direction. The components of the picker head 35 are mounted to the secondary vertical plate 82. Secondary vertical plate 82 is mounted to the vertical base frame 80 via rail 84 and linear bearings 86 for relative vertical movement. A lifting drive motor 88 (FIG. 2) is mounted to the vertical base frame 80. The lifting drive motor 88 is a servomotor that turns a drive wheel 90. A belt 92 is mounted over the drive wheel 90 and an idler wheel 94. The belt 92 is clamped to the linear bearing 86 for the secondary vertical plate 82 via clamp 96, see FIG. 4. The lifting drive 90 moves the secondary plate 82 and hence the components of the picker head 35 vertically.

The picker head 35 includes the gripping fingers 32A, 32B, a shucking and sensing head 70, and a clamp rod 98, see FIG. 5. While the preferred embodiment of the invention uses a pair of gripping fingers 32A, 32B, aspects of the invention may be implemented with a gripping device having a different configuration, such as a three or four sided gripping device. Referring to FIGS. 6A and 6B, intermeshing gripping jaws 72A, 72B are located at the distal ends of the gripping fingers 32A, 32B. The shucking head 70 is driven to move vertically between the gripping fingers 32A, 32B. The motion of the shucking head 70 is controlled independently of the vertical and horizontal motion of the gripping fingers 32A, 32B. The gripping jaws 72A, 72B include intermeshing V-shaped gripping surfaces that enable the gripping jaws 72A, 72B to engage the sidewalls of storage tubes having a large diameter, e.g. 16 mm, as well as storage tubes having a small diameter, e.g. 8 mm. FIG. 6A schematically illustrates a large diameter tube 74 being picked, whereas as FIG. 6B shows a small diameter tube 76 being picked. Each gripping jaw 72A, 72B includes a centrally disposed vertical slot 78A, 78B that provides ample clearance for the shucker head 70 to pass downward to the bottom surface of the gripping jaws 72A, 72B even when a small tube 76, FIG. 6B, is held within the jaws 72A, 72B. The purpose of the shucker head 70 is to drive the tube 74, 76 into a storage rack 26 and ensure that the storage tube is not stuck in the jaws. The shucker 70 facilitates proper seating of the storage tube 74, 76 in the rack 26 with the tube flush with other tubes in the rack. The shucker head 70 also serves as a sensor to determine whether the tube 74, 76 is properly present between the jaws 72A, 72B prior to closing the jaws 72A, 72B to pick the tube. This aspect of the invention will be discussed in more detail below.

Referring again to FIGS. 1-5, the closing and opening drive mechanism for the gripping fingers is mounted to the secondary plate 82. The drive mechanism includes a servomotor 98 that turns drive wheel 100. The upper finger base 104 of each gripping finger 32 is secured to its own linear bearing, see FIG. 5. FIG. 5 shows the linear bearing 102 for one of the gripping fingers 32A, and while the other bearing is not shown it should be understood that the construction is the mirror image of that shown in FIG. 5. The bearing 102 moves along horizontal rail 106 mounted on the secondary plate 82. The finger base 104 is also clamped to belt 108 driven by the wheel 100 so that operation of the servomotor 98 moves the gripping finger 32A horizontally to open and close jaw 72A. The upper base for the finger 32B is not visible in FIG. 5, although it should be understood that is quite similar to the base 104 shown with respect to the finger 32A except that the finger base for the finger 32B is clamped to the upper span of the belt 108. In this way, the fingers 32A and 32B open and close in unison depending on the operation of servomotor 98.

Servomotor 110 controls the vertical movement of the shucker head 70. The shucker head 70 is mounted to vertical rods and intermediate structure that pass through a guide tower 112 mounted on the secondary vertical plate 82. A header 114 for the vertical rods is exposed above the guide tower 112. The header 114 is clamped to a belt 116 that is driven by the servomotor 110 through drive wheel 118 to raise and lower the shucker head 70.

Figure 7A:
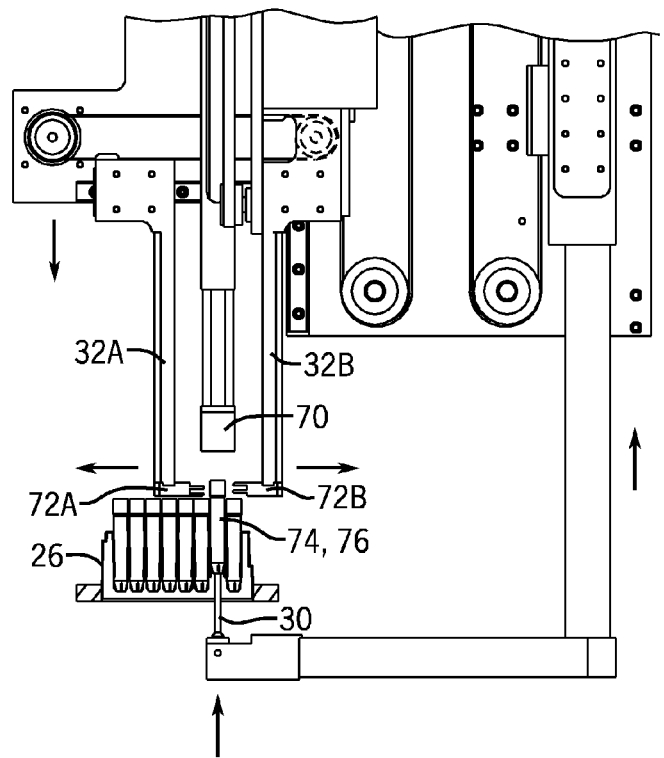
FIGS. 7A and 7B are schematic drawings illustrating the picking of a tube from a storage rack.
Figure 7B:
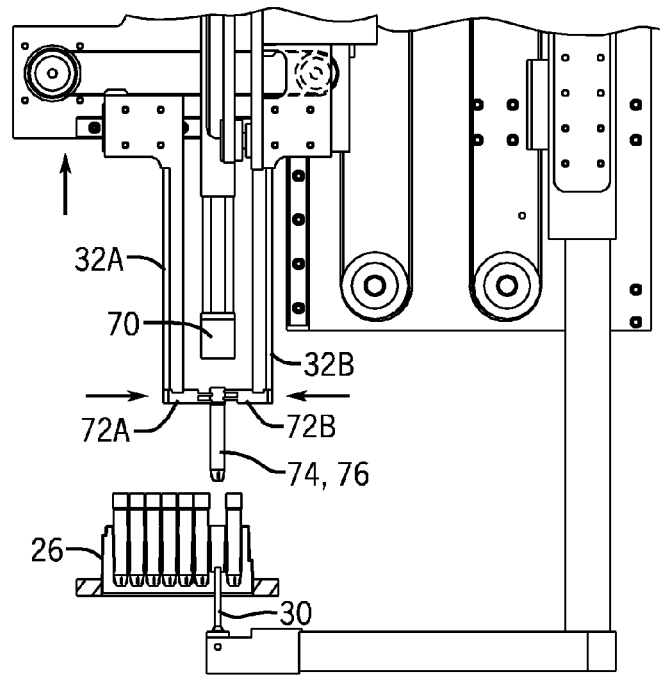

FIGS. 7A and 7B schematically illustrate the process of picking a tube from a storage rack 26. The gripping fingers 32A, 32B are positioned above the rack 26 with the gripping jaws in an open position over a selected tube location. The presenter pin 30 moves horizontally so that it is in vertical alignment with the gripping fingers 32A, 32B. As discussed previously, in the embodiment of FIGS. 1 through 10, the horizontal position of the gripping fingers 32A, 32B and the presenter pin 30 is determined by the Cartesian movement of the linear drive 38 for the picker plate assembly 28A and the linear drive 44 for the picker head 35. In the rotary embodiment shown in FIGS. 11 through 18, the storage rack is positioned in a tube picking location generally under the picker head 235 by the rotational movement of the rotary picker plate 228 and the picker head 235 moves in the horizontal X-Y plane but has less range of motion than in the Cartesian embodiment shown in FIGS. 1-10. FIG. 7A illustrates the gripping fingers 32A and 32B and the presenter pin 30 being properly aligned with the selected tube 74 in the tube rack 26. The shucker head 70 is lowered to an appropriate height, see FIGS. 6A and 6B, at which the top of the storage tube 74, 76 is expected to be present between the gripping jaws 72A, 72B when the jaws are closed to engage the tube 74, 76. The presenter pin 30 pushes upward from the bottom of the tube 74, 76 until the top of the tube 74, 76 makes contact with the bottom of the shucker head 70 (position shown in FIGS. 6A and 6B), thereby causing a change in the reading of the encoder for the servomotor 110 for the shucker drive mechanism. In this manner, the encoder for the servomotor 110 serves as a sensor to determine whether the tube is present at the appropriate height between the gripping jaws 72A, 72B before closing the jaws. If the tube 74, 76 is present at the appropriate height, then the gripping jaws 72A, 72B are closed by servomotor 98. It is preferred that servomotor 98 have a set motor torque output that is insufficient to continue further closing of the jaws 72A, 72B once the jaws firmly engage the tube 74, 76. When the gripping jaws 72A, 72B engage the sample storage tube 74, 76, the reading on the encoder for the servomotor 98 is preferably used to confirm that the diameter of the tube 74, 76 being picked matches the expected diameter for a tube at the location in the rack. Once the tube is firmly gripped by the jaws 72A, 72B, servomotor 88 operates to lift the secondary plate 82 and the picker head 35 including the gripping fingers 32A, 32B to lift the tube 74, 76 out the rack 26, as shown in FIG. 7B. It is desired that the vertical range of motion of the picker head 35 and the gripping jaws 72A, 72B be sufficient to accommodate both tall and relatively short storage tubes alike. With this in mind, it is preferred that the vertical range of motion of the picker head be at least about 7½ inches. Such a range of movement will allow for the clean picking of tubes having a height of 105 mm with ¼" clearance and will also be sufficient for tubes having a 14 mm height again with a ¼" clearance. Of course, the invention should not be limited to these dimensions. Although not shown in FIGS. 7A and 7B, the presenter push pin 30 is lowered in order to clear the rack 26 and the picker plate once the tube 74, 76 is picked.

Figure 8A:
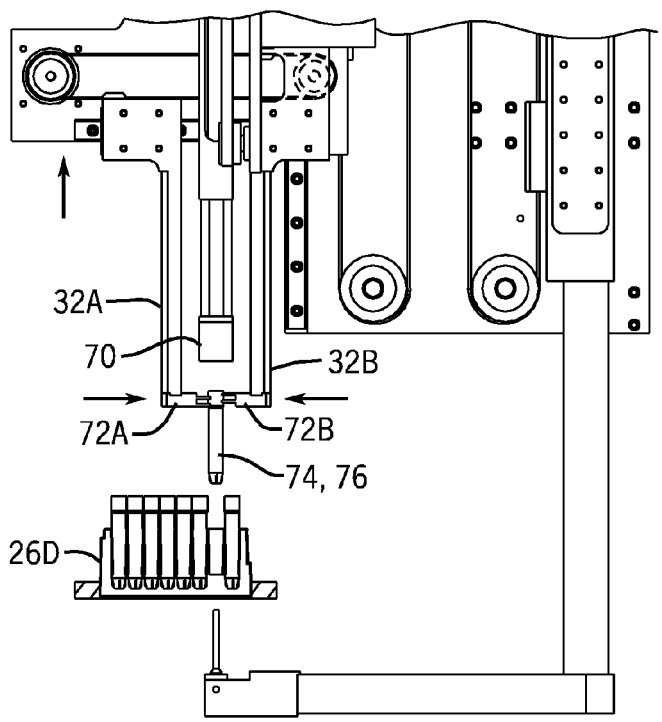
FIGS. 8A through 8D are schematic drawings illustrating the placing of a tube into a storage rack.
Figure 8B:
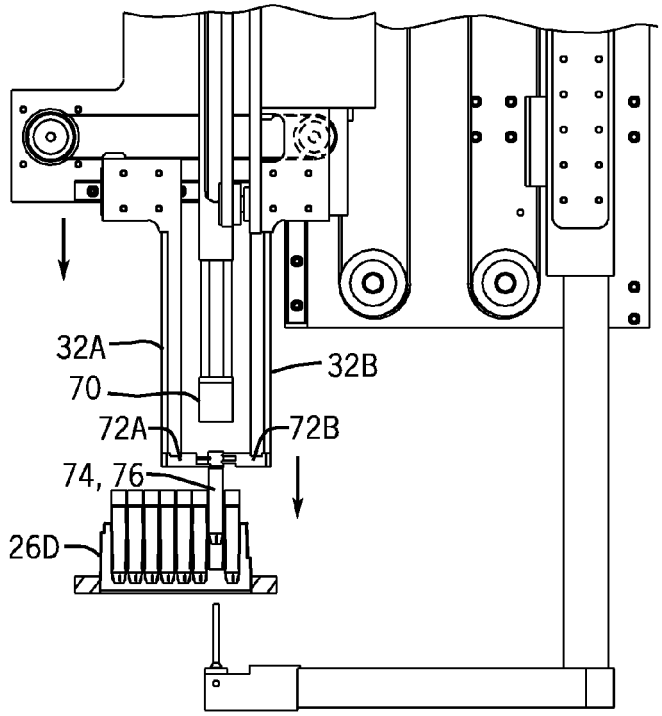
Figure 8C:
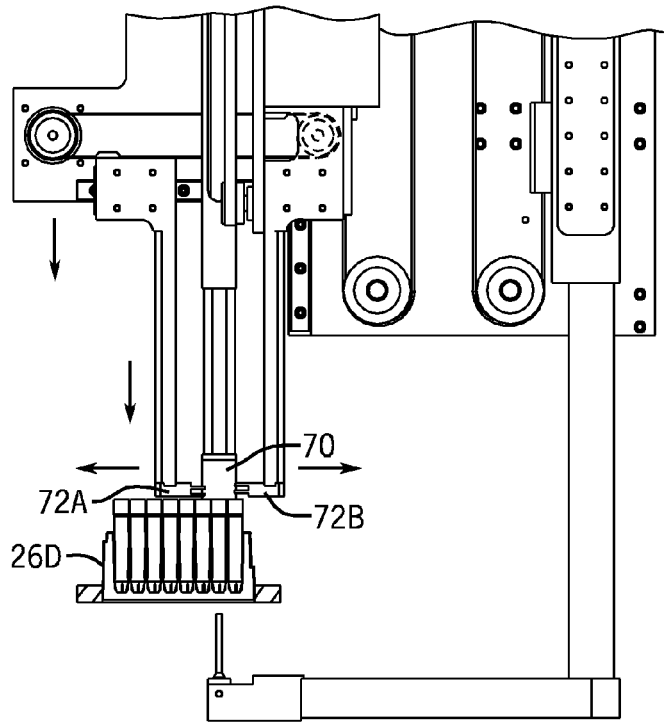
Figure 8D:
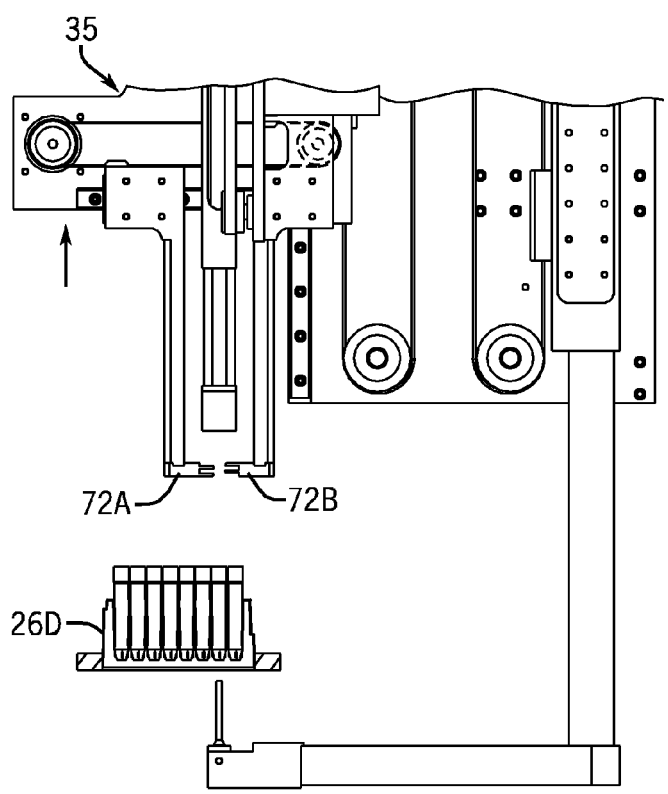

Once the tube 74, 76 is picked, it is desirable to place the tube in the destination rack or in some cases another location in the same tube rack. The tube picker can be used for the initial placement of storage samples into a storage system, for reorganizing the location of samples within the system, or for retrieval of selected samples from the system. FIGS. 8A to 8D schematically illustrate the placement of a tube 74, 76 that has been picked into a destination rack 26D. The presenter push pin 30 is not required for putting the tubes 74, 76 into the tube rack 26D. In fact, the presenter push pin 30 does not need to reach the location of the destination rack, which may be a desirable design option if dedicated receptacles are provided for destination racks in the lower compartment (either on the picker plate or otherwise). FIG. 8A shows the first step in the process in which the gripping fingers 72A, 72B and the storage tube 74, 76 are positioned over a selected receptacle in the storage rack 26D. FIG. 8B illustrates the tube 74, 76 being inserted into the receptacle in the destination rack 26D, with the gripping jaws 72A, 72B still closed to securely hold the tube 74, 76. FIG. 8C illustrates that the gripping jaws 72A, 72B have been lowered until the lower surface of the jaws is at a height flush with the top of the other storage tubes in the destination rack 26D. The gripping jaws 72A, 72B are then opened and the shucker head 70 is lowered to push the test tube into the destination rack 26D to the same height as the other tubes in the rack 26D. The shucker head 70 passes between the fingers 32A, 32B and pushes the tube 74, 76 flush with the other tubes in the rack 26D. The picker head 35 and the jaws 72A, 72B are then lifted as shown in FIG. 8D to clear the rack 26D.

It is desirable that the tube picking mechanism 10 include a clamping device for the racks 26 on the picker plate 28 to prevent racks being lifted off of the plate during the picking process. It has been found undesirable to operate mechanically complex clamping mechanisms in the ultra-low temperature, lower compartment 18. The picker head 35 shown in FIGS. 1 through 10 includes a clamp hold down rod 98 to hold the rack 26 on the picker plate 28 when picking tubes 74, 76 from the rack 26 or placing tubes in the rack. The clamp hold down rod 98 is mounted to a rotatable mechanism that allows the circumferential placement of the clamp hold down rod 98 in a wide variety of locations around the periphery of the zone in which the gripping fingers 32A, 32B are located. Such a device can be used to hold down a wide variety of storage racks having different configurations without the need to have complicated mechanical mechanisms operating in the ultra-low temperature, lower compartment 18. It is desirable that the clamp hold down rod clamp be placed at an open position on or hovering slightly above the top surface of the storage rack. When such an open position is not available, it may necessary to clamp down on or hover slightly above a tube located in the rack although such a situation is not particularly desirable. Other mechanisms such a full clamping ring, rather than a circumferentially repositionable clamp rod 98, while not preferred may perform adequately as well.

Figure 9:
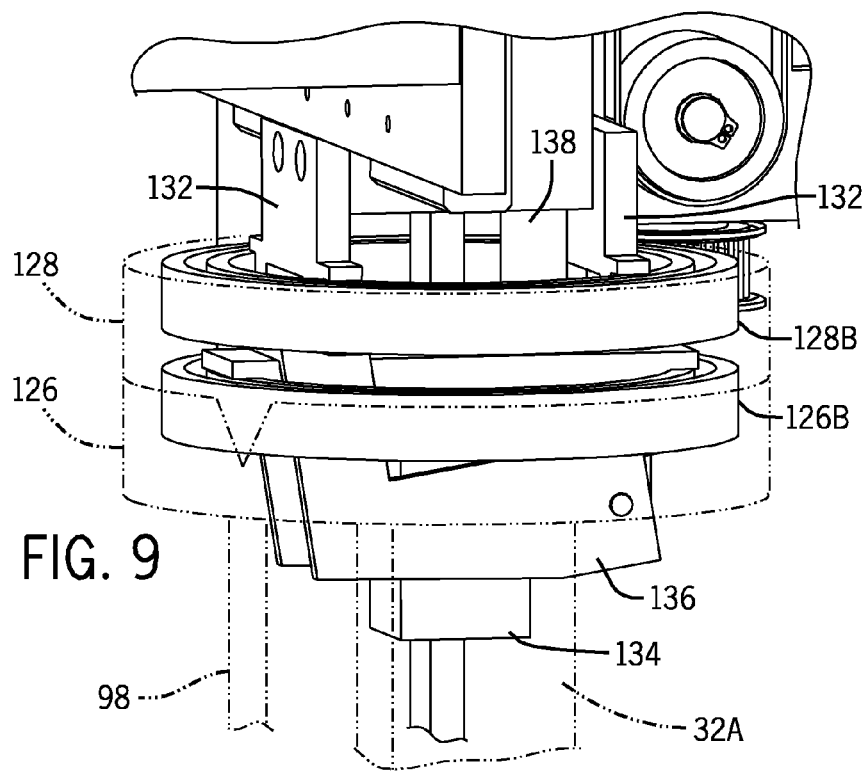
FIG. 9 is a detailed view with parts broken away of certain aspects of the clamp hold down rod mechanism.

The picker head 35 as shown in FIG. 5 includes a rotational drive mechanism for repositioning the circumferential position of the clamp hold down rod 98 and a vertical clamp drive mechanism for lowering the clamp hold down rod 98 to an appropriate hold down or clamp position. Servomotor 120 turns drive wheel 122 which in turn moves belt 124 to change the circumferential position of the hold down rod 98. The clamp hold down rod 98 extends downward from a lower collar 126. The lower collar 126 has a notch 130 that in turn engages a tab on an upper collar 128. The belt 124 rotates the upper collar 128 and, when the notch 130 in the lower collar 126 is engaged with the tab on the upper collar 128, also rotates the lower collar 126. Referring to FIG. 9, each of the collars 126, 128 has a thin wall bearing 126B, 128B, respectively, pressed into its inside surface, which allows the respective collar 126, 128 to rotate smoothly. The collars 126, 128 rotate together when the lower collar 126 is docked or engaged with the tab of the upper collar 128. The upper collar 128 is made from timing pulley stock. When the lower collar 126 is docked to the upper collar 128, the servomotor 120 drives the belt 124 to rotate the clamp rod 98 to the desired circumferential position.

Still referring to FIG. 9, the bearing 128B in the upper collar 128 is held in four places by the fingers of the two bearing mounts 132. The lower bearing 126B is held on bearing block 134 in one or more locations using a screw and nut combination. A brake arm 136 is pivotally mounted to the bearing block 134. The purpose of the brake arm 136 is to maintain the rotational position of the clamp hold down rod 98 when the lower collar 126 is disengaged from the upper collar 128. The lower collar 126 is raised and lowered by a vertical rod 138 that is pressed into the bearing block 134. To move the vertical rod 138 and engage/disengage the lower collar 126, servomotor 140 turns drive wheel 142 to move belt 144 which in turn is clamped to the vertical rod 138 via clamp 146.

Figure 10:
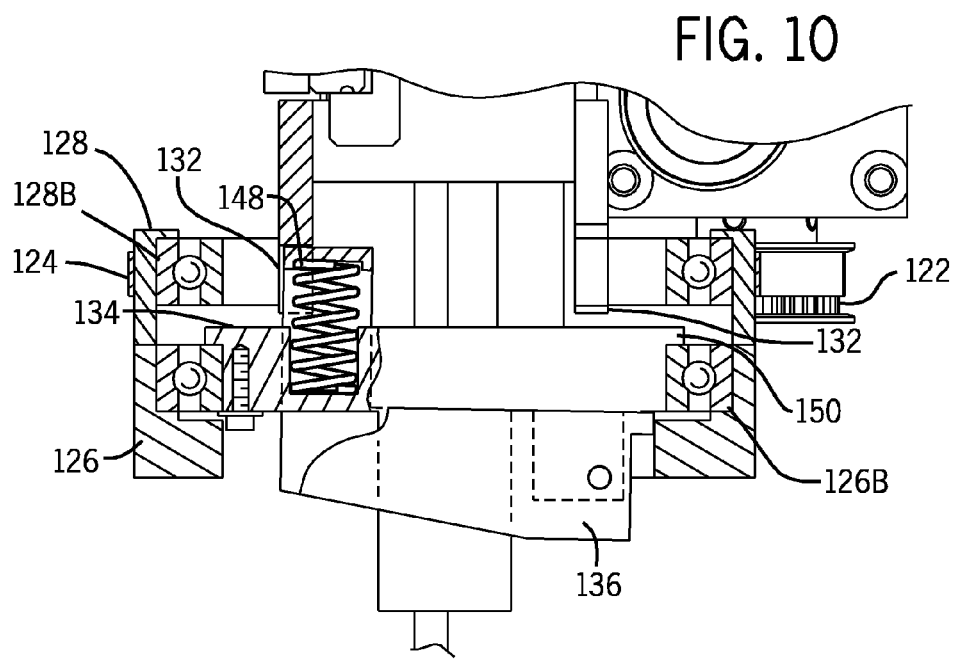
FIG. 10 is a detailed view of a braking arm for the clamp hold down rod mechanism.

Referring to FIG. 10, a spring 148 is provided at the distal end of brake arm 136. When the lower collar 126 is docked to the upper collar 128, the bearing mount 132 forces the distal end of the brake arm 136 to rotate down against the force of the spring 148 flush onto the top side of the bearing block 134. The pivoting action in turn raises a flange 150 on the other end of the brake arm 136. However, when the lower collar 126 is not docked up to the upper collar 128, as shown in FIG. 10, the spring 148 forces the distal side of the brake arm 136 upward and also forces the flange 150 downward and into engagement with an inside ledge on the lower collar 126, which prevents the lower collar 126 from rotating. The position of the pivot point on the brake arm 136 provides the spring with additional leverage for braking. When the lower collar 126 is raised and docked with the upper collar 128, the spring 148 is compressed, and the flange 150 on the brake arm 136 is released thereby allowing the lower collar 126 to rotate.

Figure 11:
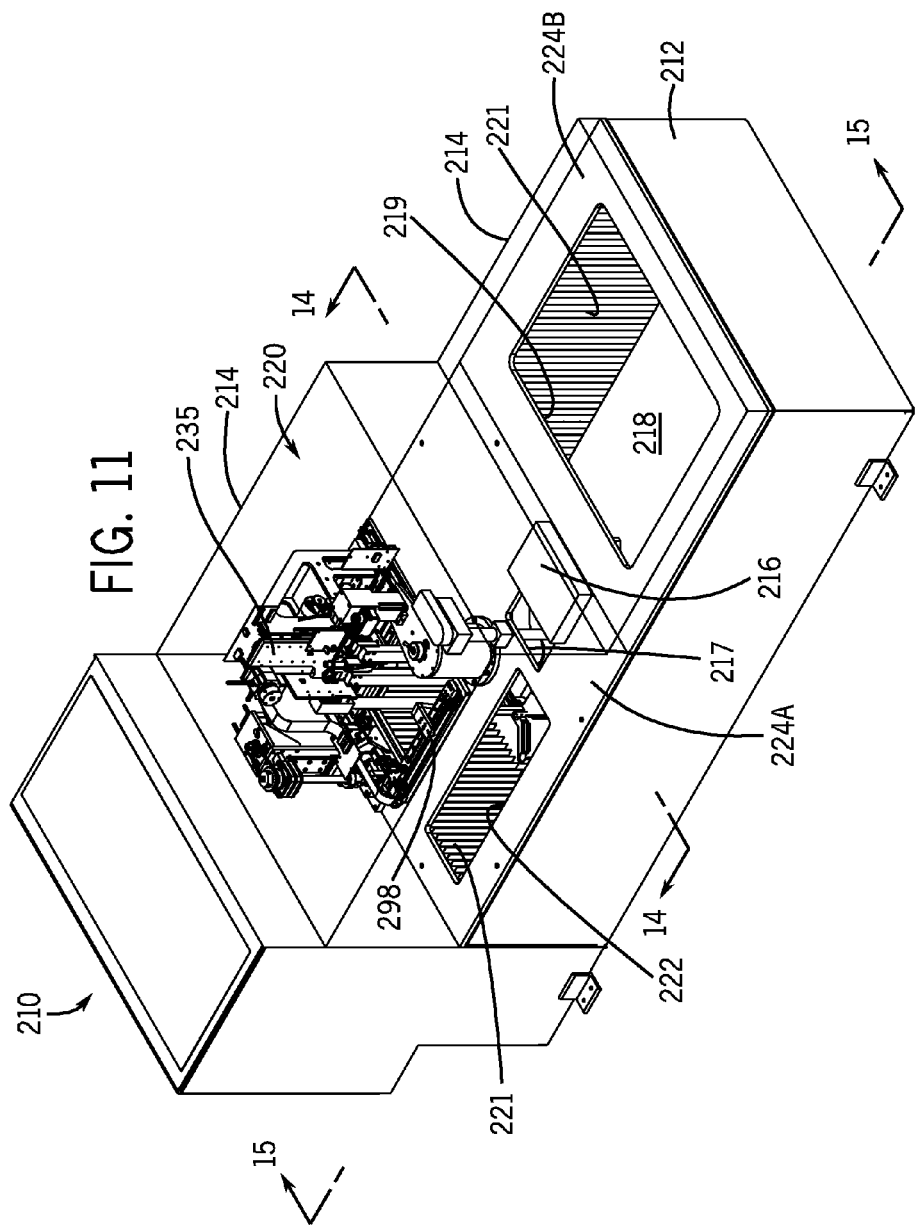
FIG. 11 is a perspective view of a tube picking mechanism constructed in accordance with a second embodiment of the invention.

FIGS. 11 through 18 illustrate a tube picking mechanism 210 that is constructed in accordance with a second embodiment of the invention. In many respects, the tube picking mechanism 210 shown in FIGS. 11 through 18 is similar to the tube picking mechanism 10 illustrated in FIGS. 1 through 10. The tube picking mechanism 210 illustrated in FIGS. 11 through 18, however, has a rotary picker plate 228, a universal clamping mechanism 298, and an enlarged refrigerated chamber 210. Enlarging the refrigerated chamber 210 is an optional feature. In a general sense, these are the primary differences over the embodiment described in FIGS. 1 through 10. Referring briefly to FIG. 11, the tube picking mechanism 210 includes a vapor barrier 214 that encloses an upper compartment 220 (see FIG. 14) in which the temperature is kept warmer than the ultra-low or cryogenic temperature in the lower compartment 218 (see FIG. 14). The lower compartment 218 in refrigerated chamber 212 is large enough to accommodate a second tube picking device 210 if desirable. Alternatively, the additional space within the lower chamber 218 can be used as cold cache for storing plates at an ultra-low temperature or cryogenic temperature on a temporary basis as needed. The opening 219 is made sufficiently large for a transport robot to place or retrieve storage racks throughout the compartment 218. Although not shown in FIG. 11, if the excess space in the lower compartment 218 is used for storage, an insulated door is placed over the opening 219 in the top surface of the chamber 212. Note that the walls of the lower compartment 218 include cooling fins 221 to facilitate efficient heat transfer when refrigerating the compartment 218. As in the previous embodiment, the opening 219 should be located on the top surface of the refrigerated compartment 218 so that the phenomenon of thermal stratification helps maintain the cold air within the lower compartment 218 when the door (not shown) is removed. In any event, it is desirable that the door (not shown) be replaced quickly in order to minimize heat transfer into the refrigerated lower compartment 218.

In the embodiment shown in FIG. 11, the partition between the upper 220 and lower 218 chambers consist of two plates 224A, 224B. The tube picking components in FIG. 11 are mounted on plate 224A. In the event that the unit includes a second tube picking device 210, a plate as configured as plate 224B would be replaced with a plate configured as plate 224A.

Figure 15:
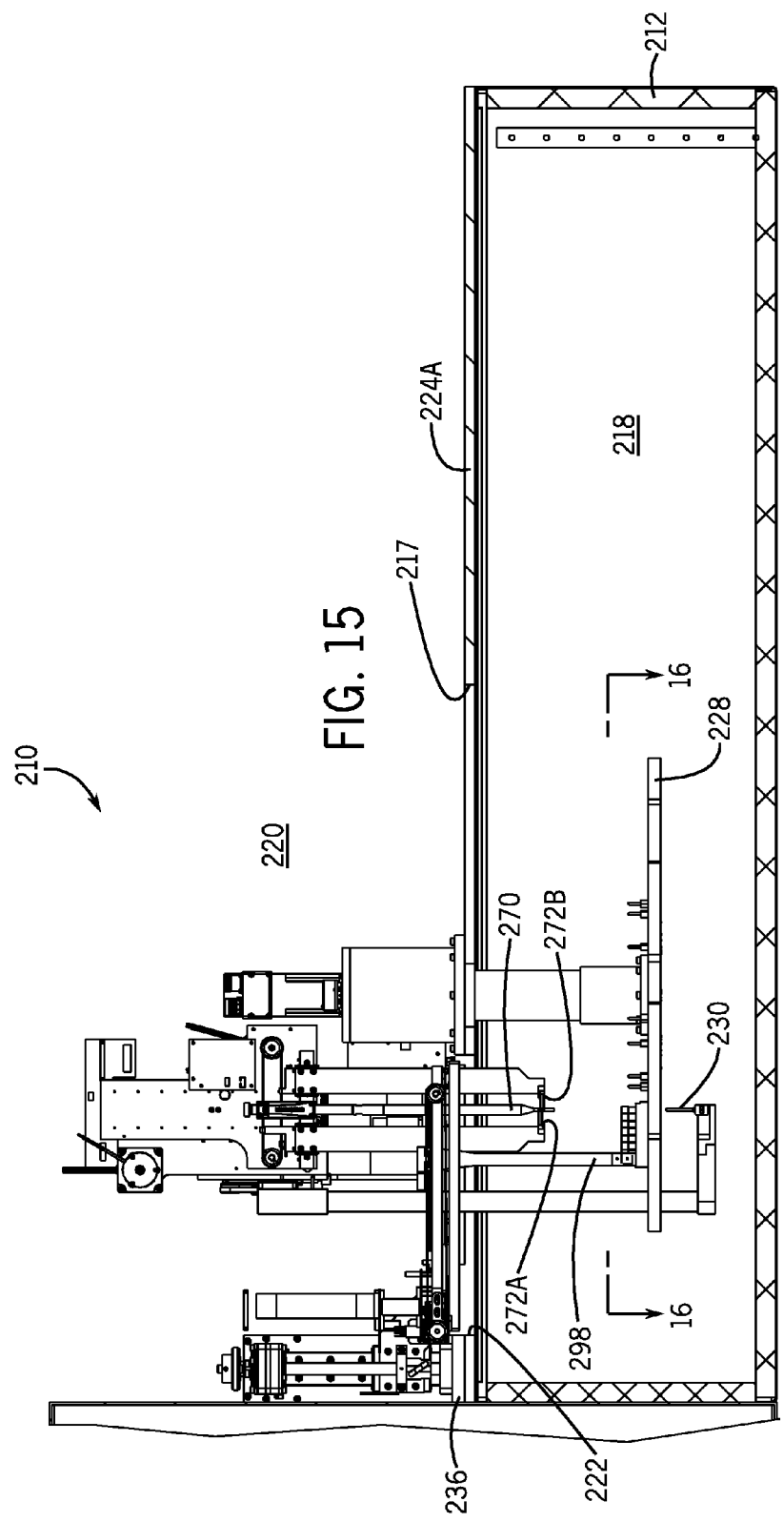
FIG. 15 is a sectional view of the tube picking mechanism with a rotary picker plate taken along line 15-15 in FIG. 11.

Plate 224A includes an opening 217 which serves as the primary opening to allow the system rack robot to place and retrieve tube storage racks from the rotary picker plate 228, see for example FIG. 15. The door 216 covers the opening 217 when storage plates are not being placed into or removed from the rotary picker plate in the lower compartment 218. FIG. 11 also shows a larger opening 222 in plate 224A. Again, an insulated door (not shown) covers the opening 222 under normal operation. The purpose of the opening 222 is to allow access into unused portions of the chamber 218 for the purpose of storing tube racks in a cold environment. The storage cache associated with opening 222 may be desirable as a practical matter in a case where the unit includes a second tube picker 210. In the embodiment shown in FIG. 11, the vapor barrier 214 covering both sides of the unit has a height sufficient to provide clearance above the tube picking mechanism 210 above plate 224A, but has a reduced height over plate 224B. While the vapor barrier 214 is not shown in all of the Figures, it should be understood that the unit 210 includes a vapor barrier 214 even if not shown.

Figure 12:
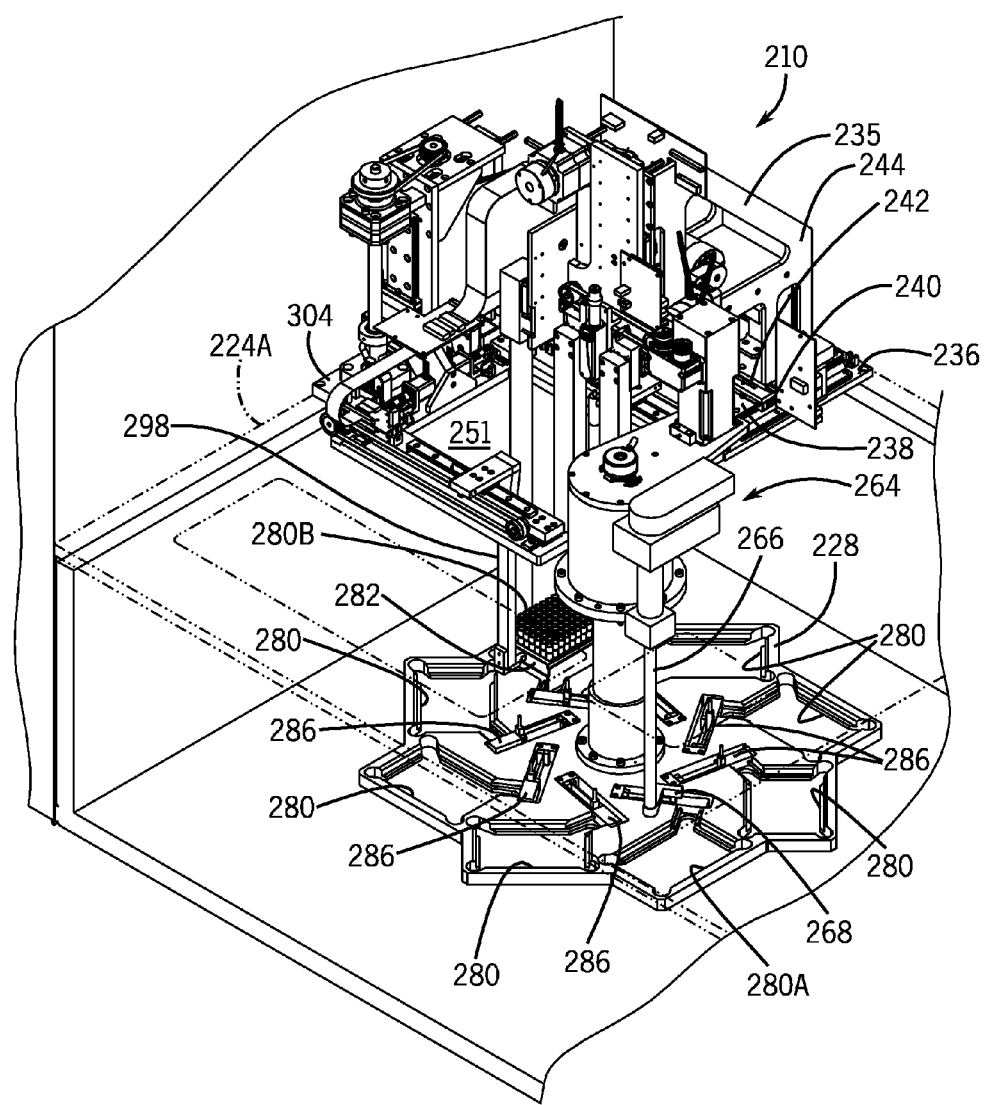
FIG. 12 is a perspective view of the internal components of the tube picking mechanism illustrated in FIG. 11, which shows the tube picking mechanism to have a rotary picker plate.
Figure 13:
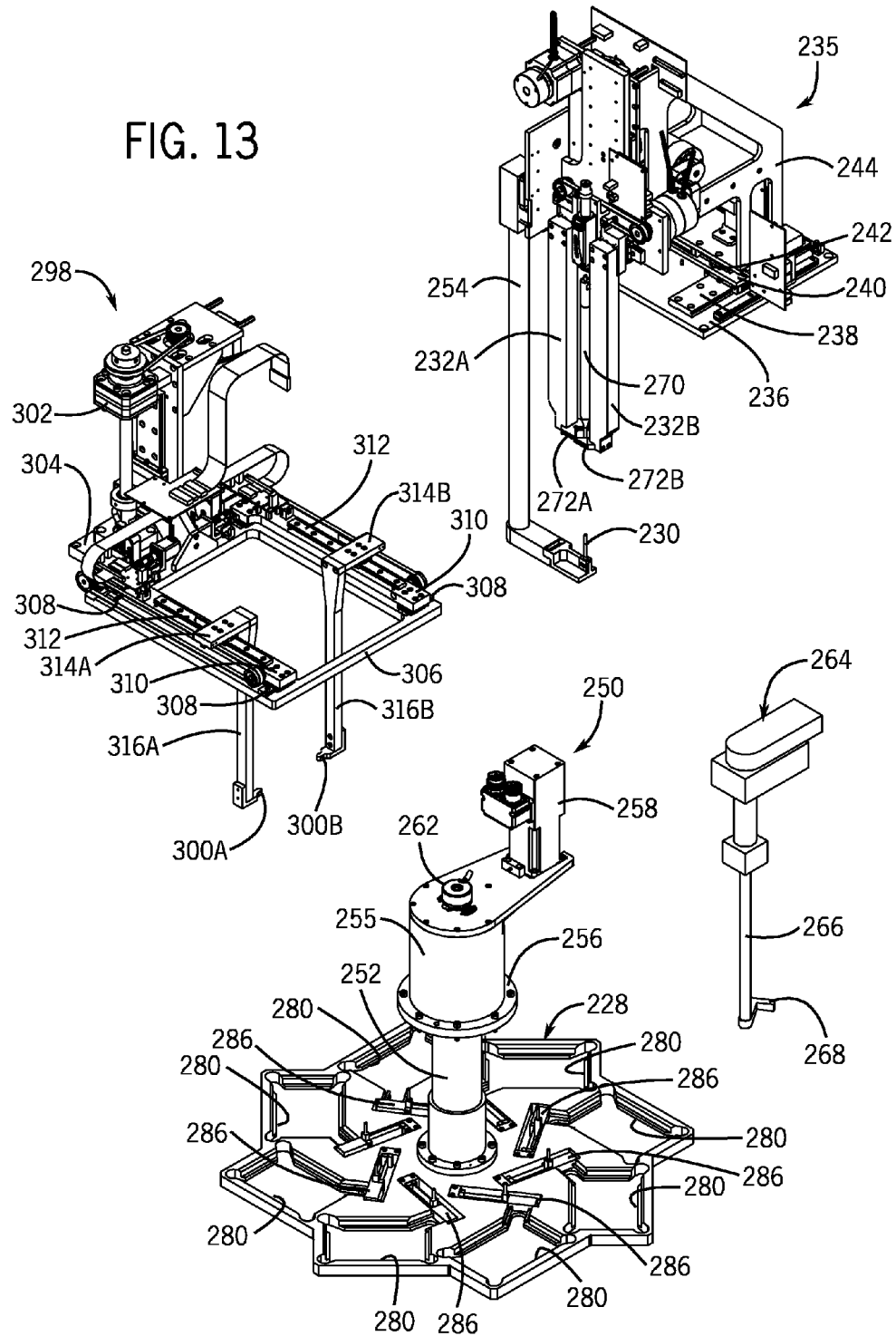
FIG. 13 is an exploded view showing various major components of the tube picking mechanism illustrated in FIGS. 11 and 12; namely a picker head, a rotary picker plate, and a rack clamp.
Figure 14:
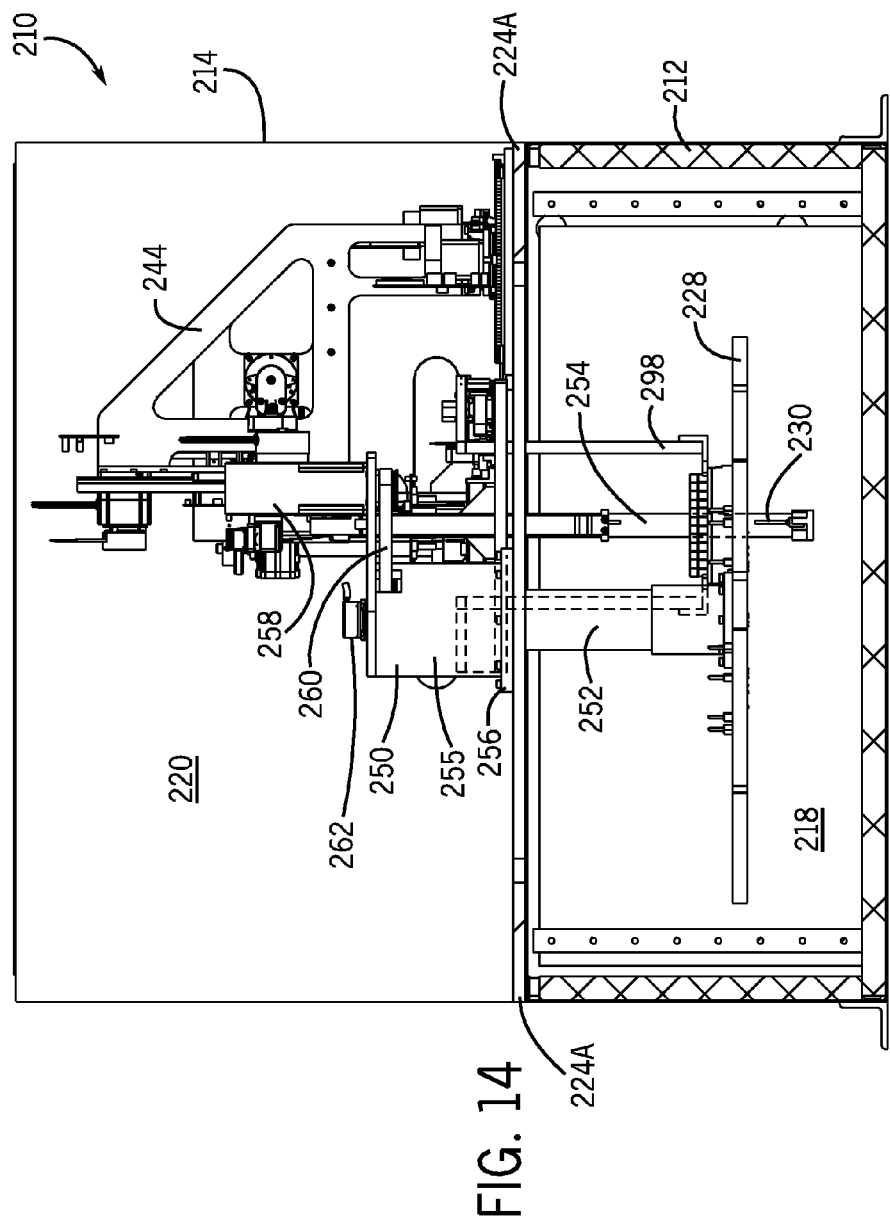
FIG. 14 is a sectional view of the tube picking mechanism having a rotary picker plate as taken along line 14-14 in FIG. 11.

The tube picking head 235 is quite similar in the rotary tube picking mechanism 210 as the tube picking head 35 in the Cartesian embodiment 10 shown in FIGS. 1-10. The primary differences are that the range of movement of the picking head 235 in the X-axis and Y-axis directions is significantly less due to the use of the rotary picker plate 228 instead of a Cartesian picker plate. The other significant difference is that the clamp mechanism 298 in the rotary embodiment 210 is separate and driven independently from the tube picking head 235. Referring now to FIGS. 12-15, the drive mechanisms for the picking head 235 are mounted on a base plate 236 which in turn is mounted to the partition plate 224A forming the boundary between the upper chamber 220 and the lower chamber 218. The arms 232A, 232B for the gripping fingers 272A, 272B and arm 254 for the presenter pin 230 pass through an opening 251, FIG. 12, in the partition plate 224A separating the upper compartment 220 from the lower compartment 218. The opening 251 in the rotary embodiment 210 is much smaller than the opening required for the Cartesian embodiment. Referring now in particular to FIG. 13, a pair of bearing rails 238 (only one shown) for Y-axis motion of the picker head 235 are mounted on base plate 236. A pair of linear bearings riding on the Y-axis rails 238 are mounted on the bottom side of a cross support 240. An X-axis rail 242 is mounted to the top surface of the cross support 240, and linear bearings riding on the rail 242 are mounted to the bottom surface of the support frame 244. X-axis and Y-axis axis belt drives driven by servomotors substantially as discussed above in connection with the prior embodiment to move the picker head 235 in the X-axis and Y-axis direction along the rails 238, 242.

The rotary picker plate 228 is driven by a rotary drive 250 located in the upper compartment 220, which drives a rotary drive shaft 252. The rotary drive shaft 252 extends upward from the rotary picker plate 228 through the partition plate 224A separating the upper compartment 220 from the lower compartment 218. The rotary shaft 252 is desirably made of a non-thermally conductive material such as amorphous polyetherimide (PEI) which is a high strength plastic having a thermal rate of contraction comparable to stainless steel. The part of the rotary drive shaft 252 residing in the upper compartment 220 is contained within drive housing 255. An annular flange 256 at the base of the drive housing 255 is attached to the partition plate 224A to secure the rotary drive to the tube picking mechanism 210. Motor 258 in the upper compartment 220 drives belt drive 260 (FIG. 14) which in turn drives a pulley located within the drive housing 255. The pulley in the housing 255 turns the top end of the rotary shaft 252 to reposition the rotary picker plate 228. Encoder 262 is used to directly monitor the location of the rotary shaft 252. Referring still to FIGS. 12 and 13, the system 210 includes a motorized release mechanism 264 that includes a motorized rotary drive that rotates an insulated shaft 266 extending downward into the lower compartment 218 for the purpose of rotating wand 268 also located in the lower compartment 218. The operation of the release mechanism 264 is described below in connection with FIGS. 16-18.

Figure 16:
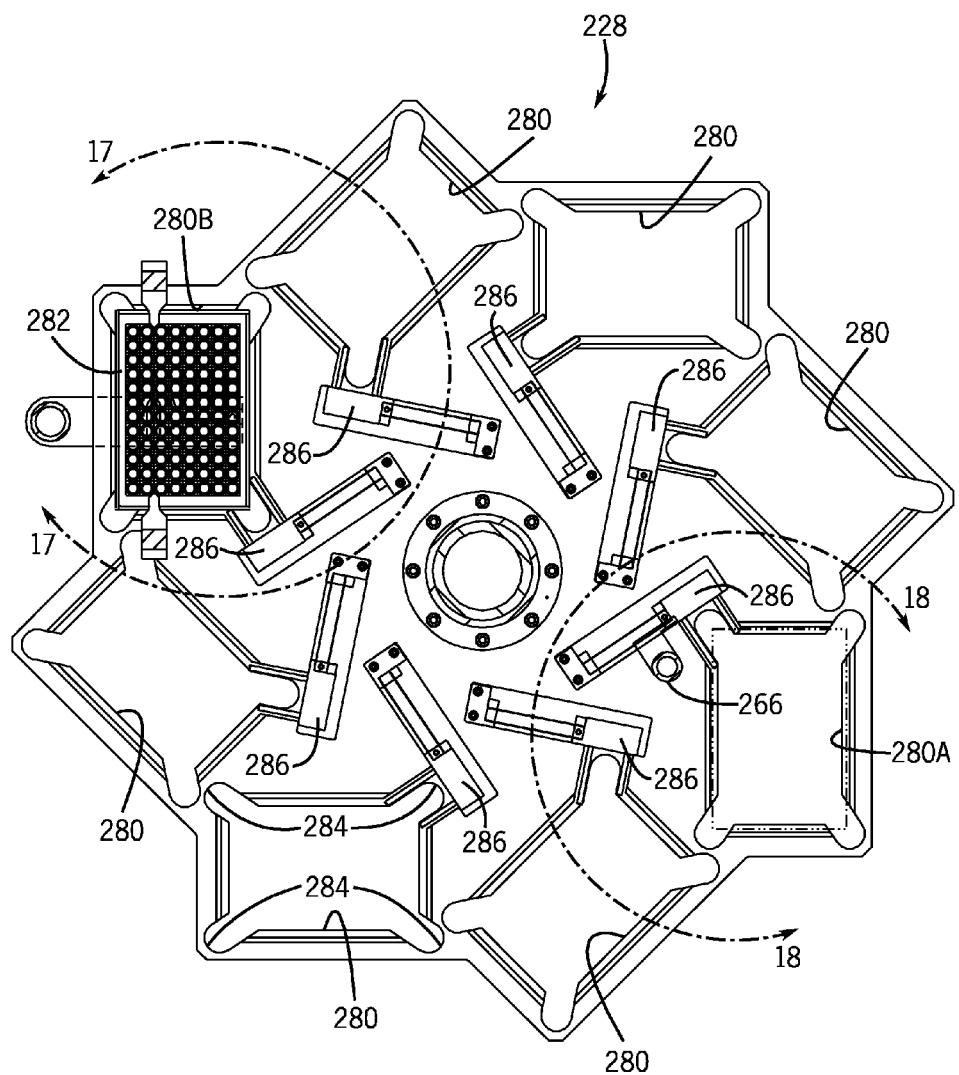
FIG. 16 is a top view of the rotary picker plate taken along line 16-16 in FIG. 15.
Figure 18:
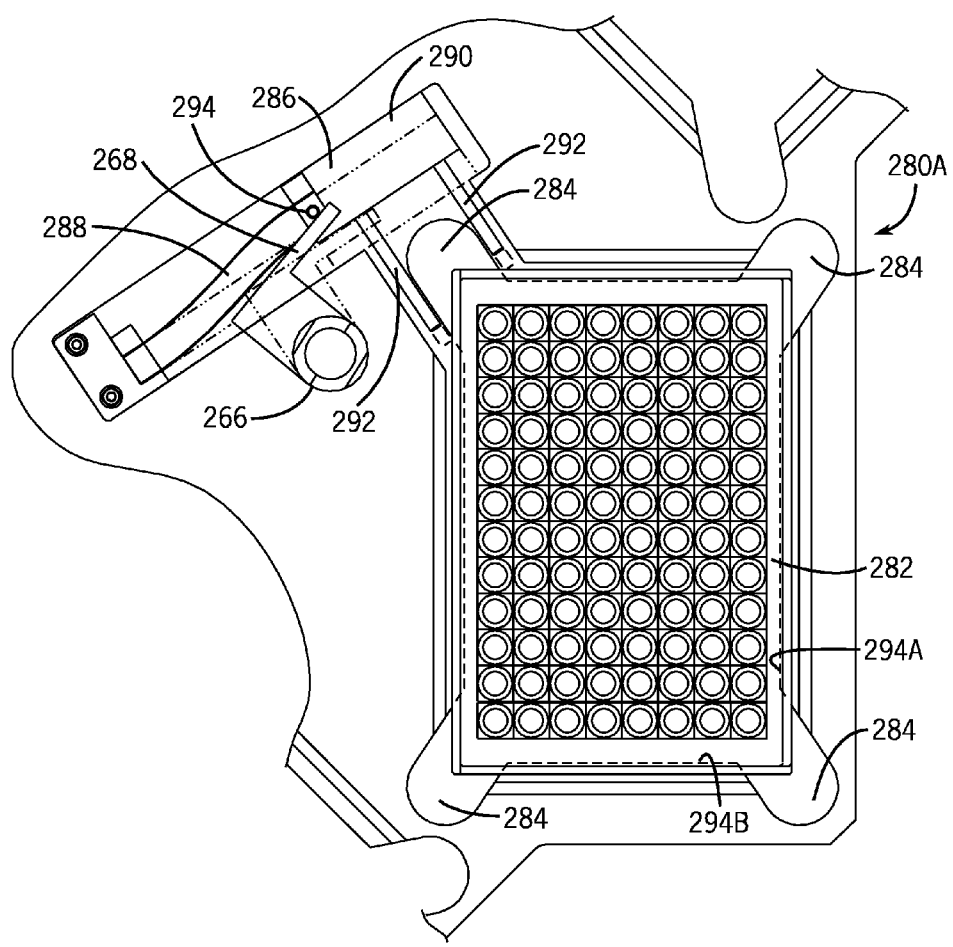
FIG. 18 is a detailed view of a rack located on the rotary picker plate at the loading position.

FIG. 16 is a top view of the rotary picker plate 228. The rotary picker plate 228 is preferably made of aluminum inasmuch it is a relatively light, durable material with known thermal contraction at ultra-low and cryogenic temperatures. Using a heavier material would require the use of a larger, more robust rotary drive. The rotary picker plate 228 includes multiple rack nesting locations 280, 280A, 280B, each for holding a tube storage rack 282. The exemplary embodiment 210 includes eight nesting locations 280 on the rotary picker plate 228. The location labeled 280A in FIG. 16 is located below robot access opening 217 and door 216 as shown in FIG. 11 and is the rack loading and retrieval position. The system rack robot places the tube rack 282 in the nest 280 that is in the location 280A below the opening 217, and also removes racks 282 from that location 280A. Note that each of the nests 280 has a generally rectangular shape in order to accommodate SBS format tube storage racks. Clearance bays 284 are located at each corner of the nest 280. The clearance bays 284 provide room for the system rack robot arms to set the respective storage rack 282 in the respective nest 280 and retract upward through opening 217 in the partition plate 224A. Referring in particular to FIG. 18, a corner reference mechanism 286 is associated with each nesting location 280. The corner referencing device 286 is a passive biasing mechanism, preferably having a block 290 attached to spring 288, and push bars 292 extending from the block 290 towards the storage rack 282 in the nest 280. An upwardly extending pin 294 is attached to the block 290. The wand 268 for the release mechanism 264, 266 engages the upwardly extending pin 294 to move the block 290 and the push bars 292 against the bias of the spring 288 and away from the nesting location 280, thus allowing clearance for the placement of a storage rack 282 in the nest 280. When the wand 268 is rotated in the clockwise direction, the force of the spring 288 pushes the block 290 and the push bars 292 against the rack 282 and in turn pushes the rack 282 into alignment with the far corner walls 294A, 294B of the nest 280 to seat the rack 282 in the proper location in the nest 280. It has been found that thermal contraction of storage racks can be considerable and can vary greatly when the racks made from different types plastic are cooled to ultra-low or cryogenic temperatures. The biasing force of the corner reference mechanism 286 holds the racks 282 securely within the respective nest 280 despite dimensional differences, and as mentioned secures the rack 282 in a known location. Once the storage rack 282 is placed in the respective nest 280, the rotary picker plate 228 rotates to bring the storage rack 282 to the picking location 280B, as shown in FIG. 16. The tube picking location 280B is located underneath the opening 251 in the top partition 224A, see FIG. 12.

Figure 17:
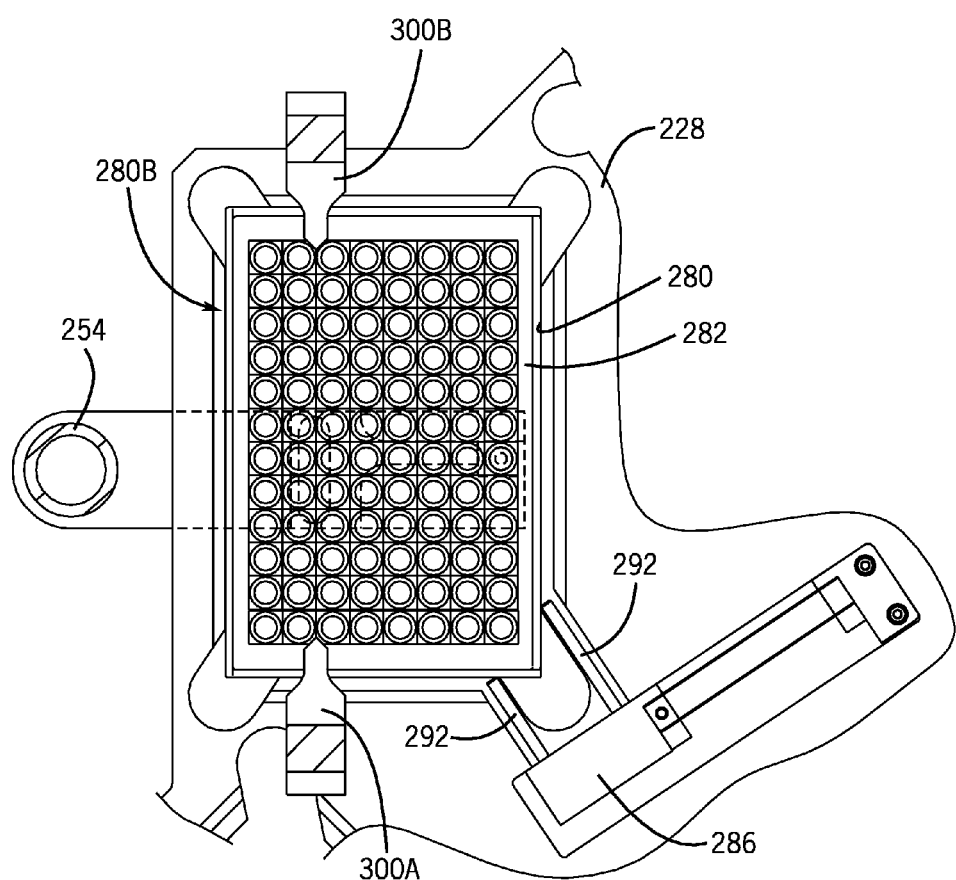
FIG. 17 is a detailed view of a rack located on the rotary picker plate under the picking head.

Referring again to FIGS. 12 and 13, the clamp mechanism 298 is separate in this embodiment from the picking head 235. The clamp mechanism 298 includes clamp feet 300A, 300B that are independently positionable in X-axis and Y-axis positions. The clamping feet 300A, 300B are designed to be located in a horizontal plane at independent X-axis and Y-axis locations suitable for clamping against the top surface or preferably hovering slightly above the top surface of the storage rack 282 from which tubes are being picked. As mentioned, since the height of any given storage rack 282 is typically a known constant, the clamp feet 300A, 300B are driven in unison vertically by a Z-axis drive, see reference number 302. More specifically, the rack clamp 298 includes a base 304 that is mounted to the partition plate 224A adjacent the opening 251. Horizontal drive base plate 306 is driven vertically by the Z-axis drive 302. In FIGS. 12 and 13, the horizontal drive plate 306 is shown in a lowered position typical of when the clamp feet 300A, 300B are clamping a storage rack 282 on the rotary picker plate 228. Rather short bearing rails 308 (FIG. 13) are mounted on the horizontal drive plate 306 for Y-axis movement of the clamp feet 300A, 300B. Linear bearings are attached to the bottom surface of support plates 310 and ride on the Y-axis rails 308. Longer X-axis bearing rails 312 are mounted on top of the support plates 310. Linear bearings mounted to the bottom of clamp supports 314A, 314B are mounted to the X-axis rails 312. Thermally insulated legs 316A, 316B extend downward from the clamp supports 314A, 314B to the respective clamp feet 300A, 300B. The legs 316A, 316B are preferably made of a thermally non-conductive material such as amorphous PEI. As such, the rack clamp 298 includes independent X-axis and Y-axis drive mechanisms that are substantially similar to the drive mechanisms that have been described previously. Similarly, it is desirable that the drives include either internal encoder or external encoder feedback. In accordance with the invention, the optimum position of the clamp feet 300A, 300B for each type or model of storage rack is stored within computer memory in the system. In this way, the clamp feet 300A, 300B are able to hover slightly above an appropriate open spot on the top surface of the respective storage rack. FIG. 17 shows a detailed view of a storage rack 282 in a nest 280 on the rotary picker plate 228 the "tube picking" position 280B located below the picking head 235 and the rack clamp 298. In this position 280B, the push bars 292 for the corner reference device 286 maintain the storage rack 282 in a corner referenced position in the nest 280 and the clamp legs 300A, 300B are lowered to an appropriate clamping location hovering slightly above the top surface of the plate 282. Those skilled in the art will appreciate that the clamping mechanism 298 provides a reliable clamping scheme that allows the independent placement of the clamping feet in a variety of locations, while at the same time locates active mechanical components in the upper, warmer compartment 220 and extends only passive components into the lower, cold chamber 218.

Operation of the rotary tube picking mechanism 210 to pick a tube from a storage rack 282 is now described. Tube handling is accomplished in the lower, colder chamber 218 at a depth determined to preserve the integrity of the samples. First, door 216 is removed and the tube storage rack 282 is inserted into the lower compartment 218 and onto the rotary picker plate 228. This is accomplished by opening the corner reference mechanism 286 for the nest 280 located in position 280A which is located below the door and using the rack robot to place the plate 282 into the nest 280. The rack robot is then removed and the corner reference mechanism 286 released. Then, the picker plate 228 is rotated to a position in which the rack 282 is located underneath the picker head 235. The legs 300A, 300B on the rack clamp 298 are positioned to a preselected effective clamping location and hover with a slight gap above the storage rack 282. The primary purpose of the clamp legs 300A, 300B is to prevent the rack from moving upward when the presenting pin 230 pushes upward on the bottom of a selected target tube. If the presenter pin 230 must exert more force than the weight of the rack 282 to present the selected target tube, the clamp legs 300A, 300B will hold the rack 282 down in the nest 280. The jaws 272A, 272B of the picking head 235 are then centered over a target tube. The shucker 270 makes contact with the tube and retracts as the presenter pin 230 pushes the tube into a position to be clamped. The clamp jaws 272A, 272B close and retract upward to pull the tube from the rack 282. Then, the clamping feet 300A, 300B retract and the rotary picker plate 228 rotates to bring a destination rack into position 280A underneath the picker head 235. It is not necessary under most circumstances to clamp the plate when putting a tube into a destination rack.

The invention has been described herein in accordance with exemplary embodiments of the invention. Many aspects of the embodiments shown and described may be modified without departing from the scope and spirit of the invention. Some of these modifications have been described above; however, there may be other such modifications. For example, in the exemplary embodiments the motorized drives are permanently located in the upper, warmer compartment. It is possible within the scope and spirit of the invention for one or more of the motorized drives to be temporarily lowered into the lower ultra-low temperature (or cryogenic) compartment during operation. Even in this circumstance, it is desirable in accordance with the invention that the motorized drive be located in the warmer, upper compartment when it is not in use.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. A tube picking mechanism comprising:
   a refrigerated chamber containing a lower compartment refrigerated to a temperature of between −50° C. and −196° C. when the tube picking mechanism is in operation;
   an upper compartment having a temperature warmer than the temperature of the lower compartment when the tube picking mechanism is in operation, a bottom portion of the upper compartment being adjacent to a top portion of the lower compartment;
   a picker plate located in the refrigerated lower compartment for holding at least one tube storage rack containing sample storage tubes;
   a picker head having two or more gripping fingers extending vertically downward in the refrigerated lower compartment, said pair of gripping fingers being able to grip and lift a single tube from a receptacle in a tube storage rack located on the picker plate in the refrigerated lower compartment;
   a presenter push pin located in the refrigerated lower compartment below the picker plate and aligned vertically with the pair of gripping fingers so that sufficient upward vertical movement of the presenter push pin pushes on a bottom of a storage tube held in a tube receptacle in a tube rack on the picker plate to facilitate lifting of the storage tube from the receptacle in the tube rack by the gripping fingers on the picker head;
   a first motorized drive mechanism for opening and closing the gripping fingers located in the warmer, upper compartment at least when the gripping fingers are not in use;
   a second motorized drive mechanism for lifting and lowering the gripping fingers located in the warmer, upper compartment at least when the gripping fingers are not in use; and
   a third motorized drive mechanism for lifting and lowering the presenter push pin located in the warmer, upper compartment at least when not in use.

2. A tube picking mechanism as recited in claim 1 the third motorized drive mechanism for lifting and lowering the presenter push pin is permanently located in the warmer, upper compartment.

3. A tube picking mechanism as recited in claim 1 wherein the refrigerated chamber comprises refrigeration coils placed around the sidewalls, and the sidewalls of the refrigerated chamber, the refrigeration coils, and a bottom wall of the refrigerated chamber are encased with insulation.

4. A tube picking mechanism as recited in claim 1 wherein the tube picking mechanism is located within an environment cooled to about −20° C. to about −30° C., and the tube picking mechanism further comprises a local compressor cooling unit that dissipates waste heat of refrigeration for the refrigerated lower compartment into the about −20° C. to about −30° C. environment.

5. A tube picking mechanism as recited in claim 1 further comprising a refrigeration unit comprising at least one of a Peltier cooler, and a vortex cooler.

6. A tube picking mechanism as recited in claim 1 further comprising a vapor barrier enclosing the upper compartment.

7. A tube picking mechanism as recited in claim 1 further comprising a door located between the upper compartment and the lower compartment in that provides access into the refrigerated chamber order to allow robotic placement of tube racks from outside of the tube picking mechanism into the refrigerated lower compartment and to allow robotic retrieval of tube racks from within the refrigerated lower compartment to outside of the tube picking mechanism.

8. A tube picking mechanism as recited in claim 1 further comprising a picker plate drive mechanism in the warmer, upper compartment for moving the picker plate in the lower compartment.

9. A tube picking mechanism comprising:
   a refrigerated chamber containing a lower compartment refrigerated to a temperature of between −50° C. and −196° C. when the tube picking mechanism is in operation;
   an upper compartment having a temperature warmer than the temperature of the lower compartment when the tube picking mechanism is in operation, a bottom portion of the upper compartment being adjacent to a top portion of the lower compartment;

a picker plate located in the refrigerated lower compartment for holding at least one tube storage rack containing sample storage tubes, wherein the picker plate is a rotary picker plate having at least two nesting locations for holding a tube storage rack and the tube picking mechanism further comprises a rotary drive that rotates the rotary picker plate to position the at least two nesting locations within the refrigerated, lower compartment;

a picker head having two or more gripping fingers extending vertically downward in the refrigerated lower compartment, said pair of gripping fingers being able to grip and lift a single tube from a receptacle in a tube storage rack located on the picker plate in the refrigerated lower compartment;

a first motorized drive mechanism for opening and closing the gripping fingers located in the warmer, upper compartment at least when the gripping fingers are not in use; and a second motorized drive mechanism for lifting and lowering the gripping fingers located in the warmer, upper compartment at least when the gripping fingers are not in use.

10. A tube picking mechanism as recited in claim 9 further comprising:

a presenter pushpin located in the refrigerated lower compartment below the picker plate and aligned vertically with the pair of gripping fingers so that sufficient upward vertical movement of the presenter pushpin pushes on a bottom of a storage tube held in a tube receptacle in a tube rack on the picker plate to facilitate lifting of the storage tube from the receptacle in the tube rack by the gripping fingers on the picker head; and a third motorized drive mechanism for lifting and lower the presenter pushpin, the third motorized drive mechanism being located in the warmer, upper compartment at least when not in use;

wherein each nesting location for holding a tube storage rack on the rotary picker plate includes an opening to provide access for the presenter pin to each potential tube location in a tube storage rack placed on the rotary picker plate.

11. A tube picking mechanism as recited in claim 9 further comprising a biasing corner reference mechanism associated with each nesting location on the rotary picker plate for applying biasing pressure to a tube storage rack located in the respective nesting location and position the tube storage rack in a predetermined reference position within the respective nesting location on the rotary picker plate.

12. A tube picking mechanism as recited in claim 11 further comprising a motorized release mechanism that mechanically releases the biasing corner reference mechanism from a tube storage place located in the respective nesting location on the rotary picker plate, wherein a motorized drive mechanism for the motorized release mechanism is located in the warmer, upper compartment.

13. A tube picking mechanism as recited in claim 10 further comprising a rack clamp for holding a tube storage rack on the picker plate when picking a tube from the storage rack, the rack clamp comprising a pair of independently positionable clamping feet which in use are positioned in predetermined clamping locations in a substantially horizontal plane, wherein the predetermined clamping locations are preselected for the type of storage rack in a respective nesting location on the picker plate.

14. A tube picking mechanism as recited in claim 13 wherein each clamping foot is attached to a downwardly extending leg and the rack clamp further comprises independent X-axis and Y-axis clamp drive mechanism for each leg and clamping foot and the X-axis and Y-axis clamp drive mechanisms are located in the upper, warmer compartment.

15. A tube picking mechanism as recited in claim 14 further comprising a Z-axis clamp drive mechanism that lifts and lowers the clamping feet and legs in unison, the Z-axis clamp drive being located in the upper, warmer compartment.

16. A tube picking mechanism as recited in claim 13 further comprising computer memory in which is stored predetermined clamping locations for multiple types of storage racks.

17. A tube picking mechanism as recited in claim 1 further comprising a picking head drive mechanism in the warmer, upper compartment for moving the picker head in the refrigerated lower compartment.

18. A tube picking mechanism as recited in claim 1 wherein the picker plate contains at least two locations for holding a tube storage rack, and each said location includes an opening to provide access for the presenter push pin to each potential tube location for a tube storage rack on the picker plate.

19. A tube picking mechanism as recited in claim 10 wherein the picker head further comprises a clamp rod for holding down a tube storage rack on the picker plate, said clamp rod being movable vertically and also capable of being placed at a location circumferentially spaced from the gripping fingers.

20. A tube picking mechanism as recited in claim 1 wherein the gripping fingers comprise a pair of generally parallel gripping fingers that extend vertically downward from the warmer, upper compartment.

21. A tube picking mechanism as recited in claim 1 wherein each gripping finger includes a gripping jaw that extends inward from the bottom of the respective gripping finger, the gripping jaws intermeshing with each other when fully closed in order to accommodate storage tubes with different diameters.

22. A tube picking mechanism as recited in claim 1 wherein the picker head further comprises a shucking mechanism having a shucking piston located between the gripping fingers, the shucking piston being movable vertically by a motor located in the upper compartment.

23. A tube picking mechanism as recited in claim 1 wherein a physical partition spans across at least a portion of the space between the upper compartment and the lower compartment.

* * * * *